US009823316B2

(12) United States Patent
Wang et al.

(10) Patent No.: US 9,823,316 B2
(45) Date of Patent: Nov. 21, 2017

(54) MAGNETIC BIOMEDICAL SENSORS AND SENSING SYSTEM FOR HIGH-THROUGHPUT BIOMOLECULE TESTING

(71) Applicant: Regents of the University of Minnesota, Minneapolis, MN (US)

(72) Inventors: Jian-Ping Wang, Shoreview, MN (US); Md Tofizur Rahman, Portland, OR (US); Yi Wang, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 206 days.

(21) Appl. No.: 14/352,638

(22) PCT Filed: Oct. 19, 2012

(86) PCT No.: PCT/US2012/061156
§ 371 (c)(1),
(2) Date: Apr. 17, 2014

(87) PCT Pub. No.: WO2013/059692
PCT Pub. Date: Apr. 25, 2013

(65) Prior Publication Data
US 2014/0292318 A1    Oct. 2, 2014

Related U.S. Application Data

(60) Provisional application No. 61/549,035, filed on Oct. 19, 2011.

(51) Int. Cl.
*G01R 33/09* (2006.01)
*C12M 3/00* (2006.01)
(Continued)

(52) U.S. Cl.
CPC .............. *G01R 33/12* (2013.01); *B82Y 25/00* (2013.01); *G01N 27/72* (2013.01);
(Continued)

(58) Field of Classification Search
CPC ....................................................... G01R 33/09
(Continued)

(56) References Cited

U.S. PATENT DOCUMENTS 6,743,639 B1    6/2004  Tondra et al.
8,076,161 B2   12/2011  Ikeda
(Continued)

FOREIGN PATENT DOCUMENTS

CN         1625686      6/2005
CN       101004416      7/2007
(Continued)

OTHER PUBLICATIONS

Baselt et al., "A Biosensor Based on Magnetoresistance Technology," Biosensors Bioelectronics, vol. 13 (7-8), Oct. 1998, pp. 731-739.
(Continued)

*Primary Examiner* — Bot Ledynh
(74) *Attorney, Agent, or Firm* — Shumaker & Sieffert, P.A.

(57) ABSTRACT

A magnetic biosensor can include a magnetic stack comprising a free layer, a fixed layer, and a nonmagnetic layer between the free layer and the fixed layer. At least one of the free layer or the fixed layer may have a magnetic moment oriented out of a major plane of the free layer or the fixed layer, respectively, in an absence of an external magnetic field. The magnetic biosensor also may include a sample container disposed over the magnetic stack, a plurality of capture antibodies attached to a bottom surface of the sample container above the magnetic stack, and a magnetic
(Continued)

field generator configured to generate a magnetic field substantially perpendicular to the major plane of the free layer or fixed layer.

14 Claims, 37 Drawing Sheets

(51) Int. Cl.
*G01R 33/12* (2006.01)
*B82Y 25/00* (2011.01)
*G01N 35/00* (2006.01)
*G01N 27/72* (2006.01)
*G01R 3/00* (2006.01)

(52) U.S. Cl.
CPC ........... *G01N 35/0098* (2013.01); *G01R 3/00* (2013.01); *G01R 33/093* (2013.01); *G01R 33/1269* (2013.01); *Y10T 29/4902* (2015.01)

(58) Field of Classification Search
USPC .......................................................... 324/252
See application file for complete search history.

(56) References Cited

U.S. PATENT DOCUMENTS

| | | | |
|---|---|---|---|
| 8,283,183 B2* | 10/2012 | Ikeda et al. | 436/526 |
| 8,705,213 B2* | 4/2014 | Butler et al. | 360/319 |
| 8,852,957 B2 | 10/2014 | Ikeda | |
| 9,121,887 B2* | 9/2015 | Wang et al. | |
| 2002/0060565 A1 | 5/2002 | Tondra | |
| 2003/0175155 A1* | 9/2003 | Charlton | 422/61 |
| 2004/0115922 A1 | 6/2004 | Gruen et al. | |
| 2005/0087000 A1 | 4/2005 | Coehoorn et al. | |
| 2005/0106758 A1 | 5/2005 | Fukumoto et al. | |
| 2005/0244873 A1* | 11/2005 | Ikeda et al. | 435/6 |
| 2006/0194327 A1 | 8/2006 | Kahlan et al. | |
| 2006/0291108 A1* | 12/2006 | Sbiaa et al. | 360/324.12 |
| 2007/0231926 A1 | 10/2007 | Ikeda et al. | |
| 2008/0014651 A1 | 1/2008 | Bangert | |
| 2008/0311598 A1 | 12/2008 | Vossenaar et al. | |
| 2009/0009156 A1 | 1/2009 | Duric | |
| 2009/0021250 A1 | 1/2009 | Ikeda | |
| 2009/0104707 A1 | 4/2009 | Wang et al. | |
| 2009/0141410 A1 | 6/2009 | Jogo et al. | |
| 2009/0152127 A1* | 6/2009 | Kaimori et al. | 205/777.5 |
| 2009/0181464 A1 | 7/2009 | De Theije et al. | |
| 2009/0206825 A1 | 8/2009 | Boeve | |
| 2009/0244788 A1* | 10/2009 | Sato | 360/324 |
| 2010/0109657 A1 | 5/2010 | Voegeli | |
| 2010/0117641 A1 | 5/2010 | Zhou | |
| 2010/0160184 A1* | 6/2010 | Suh et al. | 506/39 |
| 2010/0213934 A1 | 8/2010 | Wang et al. | |
| 2011/0156702 A1 | 6/2011 | Kim et al. | |
| 2011/0164335 A1* | 7/2011 | Xue et al. | 360/110 |
| 2011/0211272 A1* | 9/2011 | Butler et al. | 360/55 |
| 2011/0241664 A1 | 10/2011 | Zhang | |
| 2014/0174951 A1* | 6/2014 | Beer et al. | 205/777.5 |
| 2015/0044778 A1 | 2/2015 | Wang et al. | |
| 2016/0267707 A1* | 9/2016 | Vesely et al. | 348/51 |

FOREIGN PATENT DOCUMENTS

| | | |
|---|---|---|
| CN | 100343670 C | 10/2007 |
| CN | 101046464 A | 10/2007 |
| CN | 101313218 A | 11/2008 |
| CN | 101315429 A | 12/2008 |
| CN | 101379384 A | 3/2009 |
| CN | 101438162 A | 5/2009 |
| CN | 101443674 A | 5/2009 |
| CN | 101614700 | 12/2009 |
| EP | 1469311 | 10/2004 |
| JP | 2003524781 A | 8/2003 |
| JP | 2005513475 A | 5/2005 |
| JP | 2005315678 A | 11/2005 |
| JP | 2006208295 A | 8/2006 |
| JP | 2007514932 A | 6/2007 |
| JP | 2007212233 A | 8/2007 |
| JP | 2009008663 A | 1/2009 |
| JP | 2009536352 A | 10/2009 |
| JP | 2011204344 A | 10/2011 |
| WO | 03054523 A2 | 7/2003 |
| WO | 2005047864 A2 | 5/2005 |
| WO | 2006080558 A1 | 8/2006 |
| WO | 2007129284 A1 | 11/2007 |

OTHER PUBLICATIONS deBoer et al., "An Integrated and Sensitive Detection Platform for Magneto-Resistive Biosensors," Biomedical Sensor Systems, vol. 22 (9-10), Apr. 15, 2007, pp. 2366-2370.

Ding et al., "[CoFe/Pt]xn Multilayer Films with a Small Perpendicular Magnetic," Journal of Applied Physics, vol. 97, 10J117, May 2005, 3 pp.

Ding et al., "Magneto-Resistive Read Sensor with Perpendicular Magnetic Anisotropy," IEEE Transactions on Magnetics, vol. 41(2), Feb. 2005, 6 pp.

Ding et al., "Magnetoresistive Sensors with Perpendicular Magnetic Anistotropy," Journal of Applied Physics, vol. 97, 10N704, May 2005, 3 pp.

Gaster et al., "Matrix-Insensitive Protein Assays Push the Limits ofBiosensors in Medicine," Nature Medicine, vol. 15 (11), Nov. 2009, pp. 1327-1332.

Graham et al., "Single Magnetic Microsphere Placement and Detection On-Chip Using Current Line Designs with Integrated spin Valve Sensors: Biotechnological Applications," Journal of Applied Physics, vol. 91 (10), May 15, 2002, pp. 7786-7788.

Janssen et al., "On-Chip Manipulation and Detection of Magnetic Particles for Functional Biosensors," Biosensors Bioelectronics, vol. 23 (6), Jan. 2008, pp. 833-838.

Li et al., "Nanomagnetic Competition Assay for Low-Abundance Protein Biomarker Quantification in Unprocessed Human Sera," Journal of American Chemical Society, vol. 132 (12), Mar. 1, 2010, pp. 4388-4392.

Llandro et al., "Magnetic Biosensor Technologies for Medical Applications: A Review," Medical and Biological Engineering & Computing, vol. 48 (10), Jun. 24, 2010, pp. 977-998.

Martins et al., "Challenges and Trends in the Development of a Magnetoresistive Biochip Portable Platform," Journal Magnetism and Magnetic Materials, vol. 322 (9-12), May 2010, pp. 1655-1663.

Rife et al., "Design and Performance of GMR Sensors for the Detection of Magnetic Micro beads in Biosensors," Sensors and Actuators A: Physical, vol. 107 (3), Jul. 25, 2003, pp. 209-218.

Schotter et al., "Comparison of a Prototype Magnetoresistive Biosensor to Standard Fluorescent DNA Detection," Biosenssors Bioelectronics, vol. 19 (10), May 2004, pp. 1149-1156.

Srinivasan et al., "A Detection System Based on Giant Magnetoresistive Sensors and High-Moment Magnetic Nanoparticles Demonstrates Zeptomole Sensitivity: Potential for Personalized medicine," Angew. Chern., vol. 121, Mar. 2009, pp. 2802-2805.

Tamanaha et al., "Magnetic Labeling, Detection, and System Integration," Biosensors Bioelectronics, vol. 24 (1 ), Feb. 2008, pp. 1-13.

International Preliminary Report on Patentability from counterpart International Application No. PCT/US2012/061156, dated May 1, 2014, 8 pp.

International Search Report and Written Opinion from counterpart International Application No. PCT/US2012/061156, dated Mar. 7, 2013, 11 pp.

U.S. Appl. No. 14/343,252, by Jian-Ping Wang, filed Mar. 6, 2014.

Notice of Reasons for Rejection, and translation thereof, from counterpart Japanese Application No. 2014-537321, 10 pp.

Abdi et al., "Surface Plasmon Resonance Sensing Detection of Mercury and Lead Ions Based on Conducting Polymer Composite," PLoS ONE, vol. 6, No. 9, Sep. 2011, 4 pp.

(56) References Cited

OTHER PUBLICATIONS

Butler et al., "Atomic spectrometry updated. Environmental analysis," Journal of Analytical Atomic Spectrometry, vol. 22, No. 2, The Royal Society of Chemistry Jan. 22, 2007, pp. 187-221.
Das et al., "An ultrasensitive universal detector based on neutralizer displacement," Nature Chemistry, vol. 4, Macmillan Publishers Limited, Jun. 2, 2012, pp. 642-650.
Dong et al., "Quartz Crystal Microbalance Aptasensor for Sensitive Detection of Mercury(II) Based on Signal Amplification with Gold Nanoparticles," Sensors, vol. 12, May 29, 2012, pp. 7081-7094.
Ebdon et al., "Cold vapour atomic fluorescence spectrometry and gas chromatography-pyrolysis-atomic fluorescence spectrometry for routine determination of total and organometallic mercury in food samples," The Analyst, vol. 127, No. 8, Jul. 23, 2002, pp. 1108-1114.
Fortin et al., "Intercellular heating of living cells through Neel relaxation of magnetic nanoparticles," Biophysics letter, vol. 37, Jul. 20, 2007, pp. 223-228.
Freeman et al., "Chemiluminescent and Chemiluminescence Resonance Energy Transfer (CRET) Detection of DNA, Metal Ions, and Aptamer-Substrate Complexes Using Hemin/G-Quadruplexes and CdSe/ZnS Quantom Dots," Journal of the American Chemical Society, vol. 133, No. 30, American Chemical Society, Aug. 3, 2011, 10 pp.
Gaster et al., "Quantification of protein interactions and solution transport using high-density GMR sensor arrays" Nature Nanotechnology, Nature, vol. 6, Apr. 10, 2011, pp. 314-320.
Goda et al., "A hairpin DNA aptamer coupled with groove binders as a smart switch for a field-effect transistor biosensor," Biosensors and Bioelectronics, vol. 32, Dec. 24, 2011, pp. 244-249.
Graham et al., "Magnetoresistive-based biosensor and biochips," Trends in Biotechnology, vol. 22, No. 9, Science Direct, Jul. 2, 2004, 10 pp.
Grandjean et al., "Adverse Effects of Methylmercury: Environmental Health Research Implications," Environmental Health Perspectives, vol. 118, No. 8, Aug. 2010, pp. 1137-1145.
Guo et al., "Colorimetric detection of mercury, lead and copper ions simultaneously using protein-functionalized gold nanoparticles," Biosensors and Bioelectronics, vol. 26, Apr. 2, 2011, pp. 4064-4069.
Hodnik et al., "Toxin detection by surface plasmon resonance," Sensors, vol. 9, Open access, Feb. 26, 2009, pp. 1339-1354.
Jun et al., "Nanoscaling Laws of Magnetic Nanoparticles and Their Applicabilities in Biomedical Sciences," Accounts of Chemical Research, vol. 41, No. 2, Feb. 19, 2008, pp. 179-189.
Ke et al., "A facile and highly sensitive probe for Hg(II) based on metal-induced aggregation of ZnSe/ZnS quantum dots," Nanoscale, vol. 4, No. 16, The Royal Society of Chemistry, Aug. 21, 2012, 8 pp.
Kim et al., "A Drug-Loaded Aptamer-Gold Nanoparticles Bioconjugate for Combined CT Imagine and Therapy of Prostate Cancer," ACS NANO, vol. 4, No. 7, American Chemical Society, 2010, pp. 3689-3696 (Applicant points out that, in accordance with MPEP 609.04(a), the 2010 year of publication is sufficiently earlier than the effective U.S. filing date and any foreign priority date of Apr. 17, 2014 so that the particular month of publication is not in issue.).
Koets et al., "Rapid DNA multi-analyte immunoassay on magnetoresistance biosensor," Biosensors and Bioelectronics, vol. 24, ScienceDirect, Oct. 8, 2008, pp. 1893-1898.
Kong et al., "Magnetically Vectored Nanoscapsules for Tumor Penetration and Remotely Switchable On-Demand Drug Release," Nano Letters, vol. 10, No. 12, American Chemical Society, Nov. 1, 2010, pp. 5088-5092.
Langford et al., "Toxicity of mercury," Journal of Human Hypertension, vol. 13, Stockton, Jun. 10, 1999, pp. 651-656.
Lee et al., "Colorimetric Detection of Mercuric Ion (Hg) in Aqueous Media using 2+ DNA-Functionalized Gold Nanoparticles," Angewandte Chemie International Edition, vol. 46, No. 22, Wiley-VCH, 2007, pp. 4093-4096 (Applicant points out that, in accordance with MPEP 609.04(a), the 2007 year of publication is sufficiently earlier than the effective U.S. filing date and any foreign priority date of Apr. 17, 2014 so that the particular month of publication is not in issue.).
Li et al., "Elimination efficiency of different reagents for the memory effect of mercury using ICP-MS," Journal of Analytical Atomic Spectrometry, vol. 21, No. 1, Technical Note, The Royal Society of Chemistry, Nov. 16, 2005, pp. 94-96.
Loureiro et al., "Magnetoresistive detection of magnetic bead flowing at high speed in microfluidic channels," IEEE Transactions on Magnetics, vol. 45, Oct. 10, 2009, pp. 4873-4876.
Mamiya et al., "Hyperthermic effects if dissipative structure of magnetic nanoparticles in large alternating magnetic fields," National Institute for Materials Science, Nov. 15, 2011, pp. 1-7.
Manteca et al., "GMR sensors: Magnetoresistive behavior optimization for biological detection by means of superparamagnetic nanoparticles," Biosensors and Bioelectronics, vol. 26, ScienceDirect, Nov. 24, 2010, pp. 3705-3709.
Martins et al., "Femtomolar limit of detection with a magnetoresistive biochip," Biosensors and Bioelectronics, vol. 24, Feb. 6, 2009, pp. 2690-2695.
Morel et al., "The chemical cycle and bioaccumulation of mercury," Annual review of ecology and systematics, vol. 29, 1998 pp. 543-566.
Mulvaney et al., "Magnets tackle kinetic questions," Nature Nanotechnology, vol. 6, Nature, May 2011, pp. 266-267.
Mulvaney et al., "Rapid, femtomolar bioassays in complex matrices combining microfluids and magnetoelectronics," Biosensors and Bioelectronics, vol. 23, ScienceDirect, Apr. 8, 2007, pp. 191-200.
Nam et al., "Nanoparticle-Based Bio-Bar Codes for the Ultrasensitive Detection of Proteins," Science, vol. 301, No. 5641, Reports, Sep. 26, 2003, pp. 1884-1886.
Ono et al., "Highly selective oligonucleotide-based sensor for mercury(II) in aqueous solution," Molecular sensors, vol. 43, Angewandte, 2004, pp. 4300-4302.
Osterfeld et al., "Multiplex protein assays based on real-time magnetic nanotag sensing," Proceedings of the National Academy of sciences of the United States of America, vol. 105, PNAS, Dec. 30, 2008, pp. 20637-20640.
Rajkovic et al., "Immunoquantitative Real-Time PCR for Detection and Quantification of *Staphylococcus aureus* Enterotoxin Bin Foods," Applied and Environmental Microbiology, vol. 72, No. 10, American Society for Microbiology, Oct. 2006, pp. 6593-6599.
Rosi et al., "Oligonucleotide-Modified Gold Nanoparticles for Intracellular Gene Regulation," Science, vol. 312, May 19, 2006, pp. 1027-1030.
Salgan et al., "Zeta potential and isoelectric points of biomolecules: The effects of ion types and ionic strengths," International Journal of Electrochemical science, vol. 7 Dec. 1, 2012, pp. 12404-12414.
Schotter et al., "Development of a magnetic lab-on-a-chip for point-of-care sepsis diagnosis," Magnetism and Magnetic Materials, vol. 321, ScienceDirect, Feb. 21, 2009, pp. 1671-1675.
Shao et al., "Protein typing of circulating microvesicles allows real-time monitoring of glioblastoma therapy," Nature Medicine, vol. 18, No. 12, Technical Reports, Nov. 11, 2012, pp. 1835-1843.
Srinivasan et al., "A detection system based on giant magnetoresistive sensors and high-moment magnetic nanoparticles demonstrates zeptomole sensitivity: Potential for personalized medicine," Biosensors, vol. 48, Andgewandte, 2009 pp. 2763-2767 (Applicant points out that in accordance with MPEP 609.04(a), the 2009 year of publication is sufficiently earlier than the effective U.S. filing date and any foreign priority date of Apr. 17, 2014 so that the particular month of publication is not in issue).
Stenberg et al., "Kinetics of antigen-antibody reactions at solid-liquid interfaces," Journal of Immunological methods, vol. 113, Jun. 29, 1988, pp. 3-15.
Tang et al., "Design fabrication, and performance of spin-valve read heads for magnetic recording applications," Journal of research and development, vol. 42, Jan. 1, 1998, pp. 103-116.
Tu et al., "Real-time measurements of Brownian relaxation of magnetic nanoparticles by a mixing-frequency method," Applied Physics letters, vol. 98, May 26, 2011, pp. 1-3.
Vasimalai et al., "Mercaptothiadiazole capped gold nanoparticles as fluorophore for the determination of nanomolar mercury (II) in

(56) References Cited

OTHER PUBLICATIONS aqueous solution in the presence of 50000-fold major interferents," Analyst, vol. 137, No. 14, The Royal Society of Chemistry, Jul. 21, 2012, pp. 3349-3354.

Wang et al., "Magnetic Detection of Mercuric Ion Using Giant Magnetoresistive Based Biosensing System," Analytical Chemistry, American Chemical Society, Mar. 24, 2014, 23 pp.

Wang et al., "Surface modification for protein and DNA immobilization onto GMR biosensor," IEEE transactions on magnetics, vol. 49, Jan. 1, 2013, pp. 296-299.

Xia et al., "Colorimetric detection of DNA, small molecules, proteins, and ions using unmodified gold nanoparticles and conjugated polyelectrolytes," Proceedings of the National Academy of sciences of the United States of America, vol. 107, PNAS, Jun. 15, 2010, pp. 10837-10841.

Xue et al., "One-step, room temperature, colorimetric detection of mercury (Hg2+) using DNA/nanoparticle conjugates," Journal of the American Chemical Society. vol. 130, JACS, Sep. 6, 2007, pp. 3244-3245.

Zheng et al., "Multiplexed electrical detection of cancer markers with nanowire sensor arrays," Nature Biotechnology, The Science and Business of Biotechnology, vol. 23, No. 10, Sep. 18, 2005, pp. 1294-1301.

Zhi et al., "Quick genotyping detection of HBV by giant magnetoresistive biochip combined with PCR and line probe assay," Lab on a chip, vol. 12, Miniaturisation for chemistry, physics, biology, materials science and bioengineering, Feb. 21, 2012, pp. 741-745.

U.S. Appl. No. 14/676,620, by Jian-Ping Wang, filed Apr. 1, 2015.

Decision of Final Rejection, and translation thereof, from counterpart Japanese Application No. 2014-537321, dated Jan. 12, 2016, 6 pp.

Zheng et al., "Switch-free read operation design and measurement of magnetic tunnel junction magnetic random access memory arrays," Applied Physics Letters, vol. 79, No. 17, Oct. 22, 2001, 4 pp.

Wu et al., "Research development of spin valve giant magnetic resistance biosensors with magnetic labels," Transducer and Microsystem Technologies, China Academic Journal Electronic Publishing House, Translation provided for only the abstract, Nov. 2007, 4 pp.

Second Office Action, and translation thereof, from counterpart Chinese Application No. 2016111401151580, dated Nov. 17, 2016, 15 pp.

\* cited by examiner

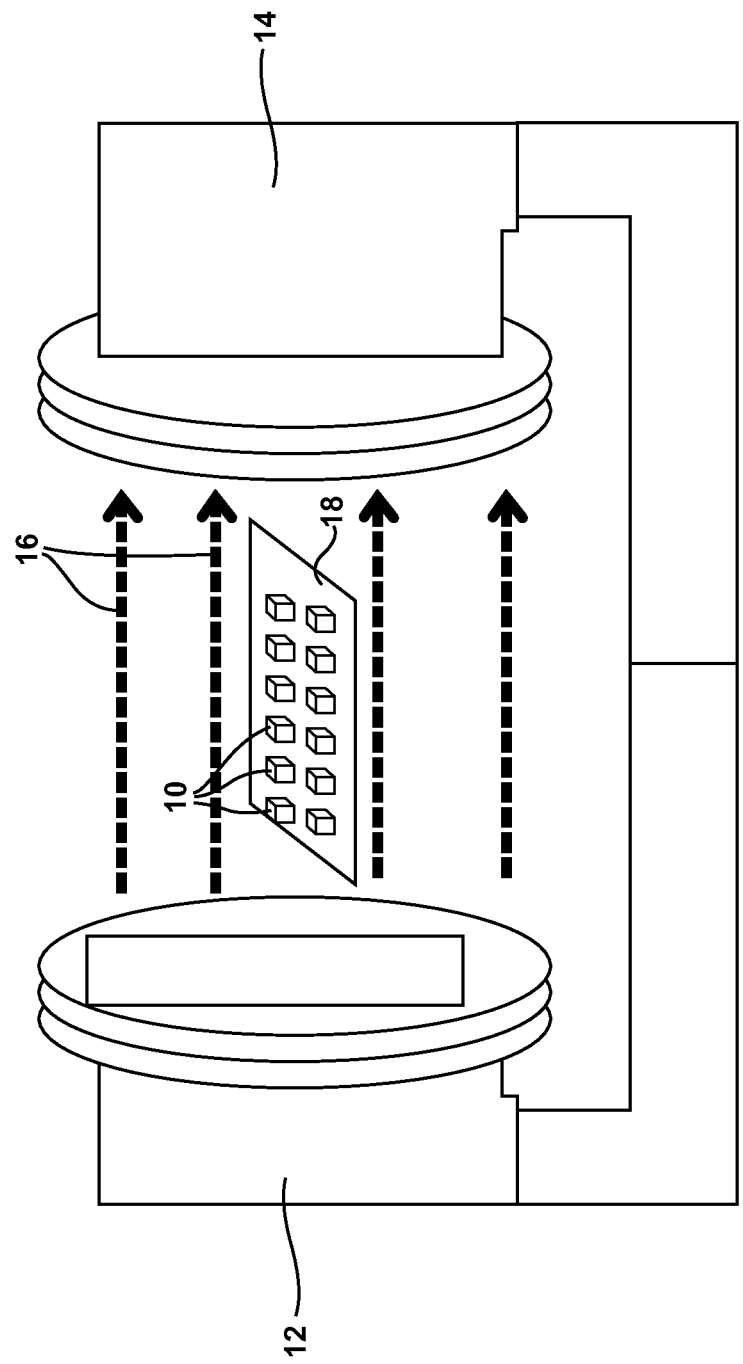

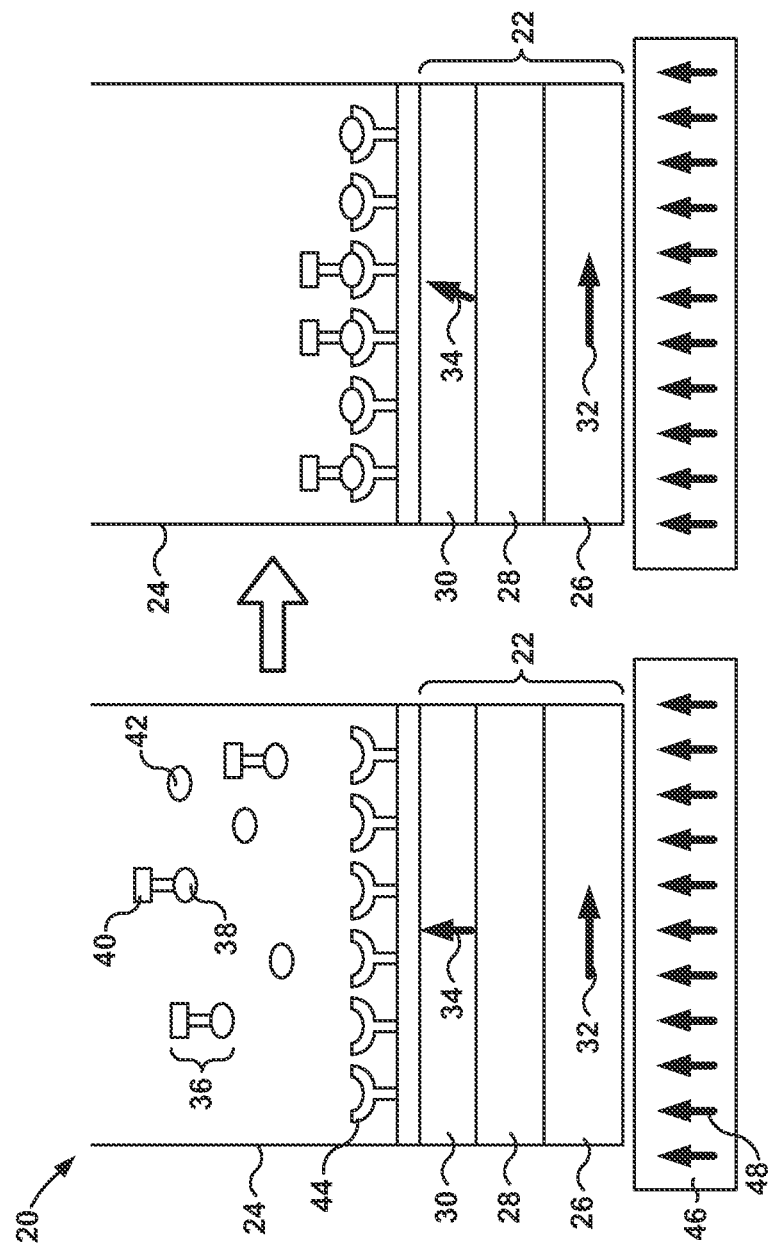

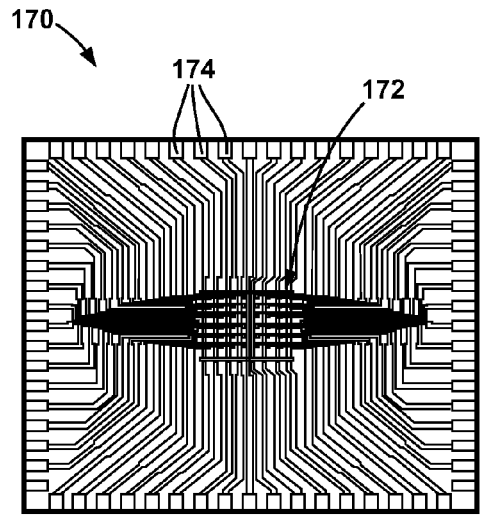 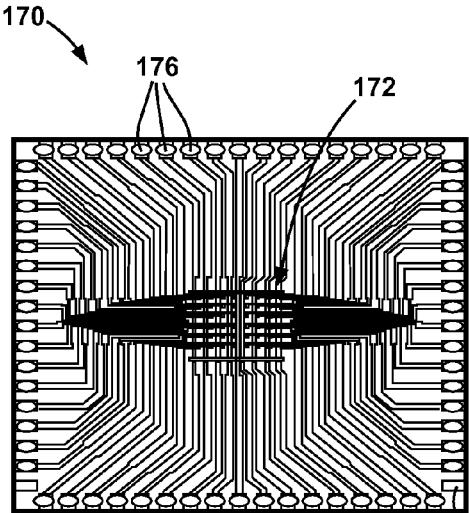
FIG. 12A    FIG. 12B
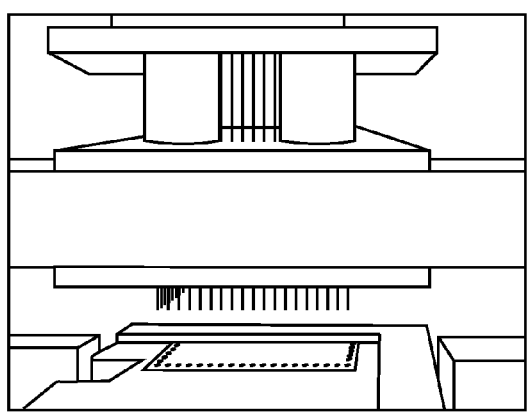 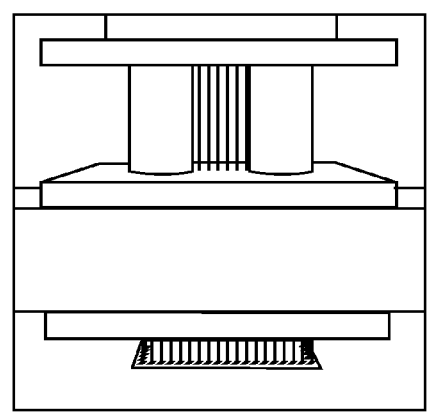
FIG. 12C    FIG. 12D

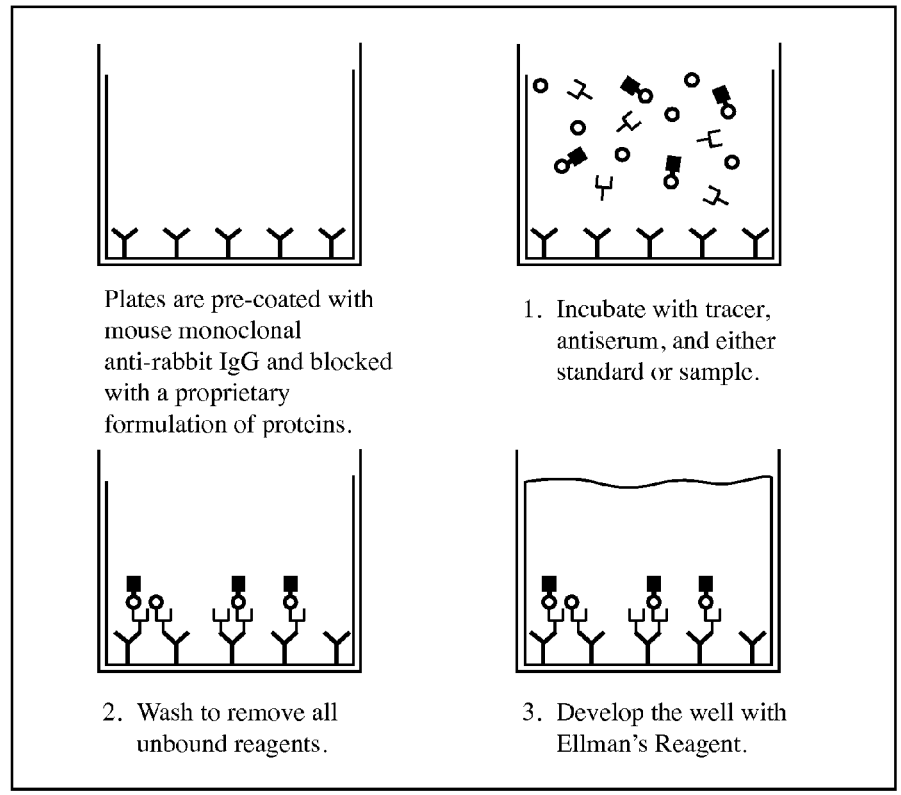
| | |
|---|---|
| o-□ | Estradiol (tracer) labeled with NMP |
|  | Specific antiserum to Estradiol |
|  | Monoclonal Anti-Rabbit IgG |
|  | Free Estradiol |
FIG. 39

MAGNETIC BIOMEDICAL SENSORS AND SENSING SYSTEM FOR HIGH-THROUGHPUT BIOMOLECULE TESTING

This application is a national stage entry under 35 U.S.C. §371 of PCT Application No. PCT/US2012/061156, filed Oct. 19, 2012, which claims the benefit of U.S. Provisional Application No. 61/549,035, entitled, "A MAGNETIC BIOMEDICAL SENSING SYSTEM AND INSTRUMENTATION FOR LARGE NUMBER OF SAMPLES AND HIGH-THROUGHPUT BIOMOLECULE TESTING," and filed on Oct. 19, 2011. The entire contents of PCT Application No. PCT/US2012/061156 and U.S. Provisional Application No. 61/549,035 are incorporated herein by reference.

TECHNICAL FIELD

The disclosure relates to systems and techniques for magnetic biomolecule sensing.

BACKGROUND

Bioassays that detect and quantify biomolecules at ultra-low concentrations are of great need in many fields, including basic medical science, disease control and diagnostics, drug discovery, and environment monitoring. Bioassays can be used for disease or pathogen detection based on specific interactions between oligonucleotides, such as DNA-DNA or RNA-RNA interactions; small-molecule-biomolecule interactions; aptamer-biomolecule interactions; protein interactions; or the like.

Magnetic biosensing techniques utilize magnetic fields to detect and quantify biomolecules. In some implementations, magnetic labels, such as magnetic nanoparticles (MNPs) or magnetic microbeads, can be attached to an analyte in a reagent. The same analyte, which is not attached to a magnetic label, may be present in a serum sample. The reagent and serum sample may be introduced into a sensor that includes a magnetic sensor and a plurality of capture molecules, which are configured to capture the analyte, e.g., using covalent or ionic bonding. The magnetic sensor may include a magnetic layer whose magnetic moment is fixed in a particular orientation (a fixed layer) and a magnetic layer whose magnetic moment is free to rotate under influence of an external magnetic field (a free layer). When an external applied field is applied to the sensor, e.g., using an electromagnet or a permanent magnet, the magnetic moment of the free layer rotates to an orientation determined by the effective magnetic field applied to the layer, which may include components from the external applied field, magnetic fields from any magnetic objects (e.g., magnetic particles above the sensor's surface, the magnetic field generated by a current that passes through the magnetic sensor during a read process, and the magnetic field generated by other magnetic layers (e.g., the fixed layer) of the magnetic sensor. The concentration of the analyte in the serum sample then may be determined using the magnetic biosensor, as the orientation of the magnetic moment of the free layer will rotate under influence of the magnetic markers when analytes bonded to magnetic markers are captured by the capture molecules. Further details of magnetic biosensors and related techniques are described in U.S. Provisional Application No. 61/534,636, incorporated herein by reference.

In some magnetic biosensors, an in-plane external magnetic field configuration is used (i.e., the external magnetic field is applied to the sensor in a direction parallel to a major plane of the free layer and fixed layer). The instrumentation and working principle for this configuration is illustrated schematically in FIG. 1. In this configuration, the sample plate 18 including one or more samples 10 is placed on one or more magnetic sensors (not shown) between two opposing magnets 12 and 14 that generate an in-plane magnetic field represented by arrows 16 (i.e., in plane relative to a major plane of the free magnetic layer). This in-plane configuration can be utilized for a limited size of testing plate (e.g., 2-5 centimeters (cm) in length), but cannot be used with large sample plates (e.g., 50 cm in length) unless large magnets 12 and 14 are used, which is not compatible with a bench top system. Large magnets are required because a uniform, relatively large (e.g., about 20 Oerstad (Oe) to about 100 Oe) in-plane magnetic field is required for accurate detection of biomolecules in the samples being tested. This configuration with large electromagnet is not only unsuitable for bench top operation but also requires large amounts of power to operate the large electromagnet.

SUMMARY

The disclosure describes a magnetic biosensing system in which an external magnetic field is applied to the magnetic sensor that is perpendicular to the major plane of the free layer and the fixed layer (a perpendicular magnetic field). Such systems may facilitate testing of a large number of samples simultaneously, because a sufficiently large, more uniform magnetic field may be applied to more sensors at one time. In some examples, using the new magnetic biosensing system, a bench top biomedical detection system can test more than thousands of samples simultaneously and within a relatively short time, such as within 5 minutes. Moreover, the magnetic biosensing system described herein may allow automatic handling of samples and testing, e.g., by a programmed robot. Prior art sensing schemes and instrumentation cannot simultaneously test such large volumes of samples.

In some implementations, the magnetic biosensing system utilizes a plurality of magnetic sensors in which (for each magnetic sensor) at least one of the free layer or the fixed layer has out-of-plane magnetic anisotropy (i.e., an easy axis of the layer is oriented out of a major plane of the layer). Additionally, the external magnetic field is applied to the magnetic sensor in a direction perpendicular to the major plane of the free layer and fixed layer. As the sample holder plate is oriented with its major plane generally parallel to the major plane of the free layers and fixed layers of the plurality of sensors, the external magnetic field is also applied perpendicular to a major plane of the sample holder plate. This arrangement places the magnet generating the external magnetic field below the sensors, which are below the sample plate. This may allow the use of a large and automatically-controlled sample plate much closer to the magnet (compared to the in-plane magnetic field configuration) and results in substantial uniformity of the magnetic field over the all the samples in the sample plate, as each sample is substantially the same distance from the magnet.

The magnetic biosensing system described herein may be used with different types of magnetic sensors, such as magnetic tunnel junction (MTJ) sensors that may have the spin valve structure, giant magnetoresistive (GMR) sensors that may have the spin valve structure, Hall sensors that may have the spin valve structure, giant magnetoimpedence (GMI) sensors, or the like. The magnetic biosensing system may utilize a multi-probe stage or station for a simple and reliable connection and disconnection of an electronic control to the magnetic sensor electrodes.

The magnetic biosensing system may magnetize and capture biomolecules with magnetic labels, such as magnetic nanoparticles (MNPs) or slightly larger magnetic particles including magnetic microbeads to a top layer or coating of the magnetic biosensor. The magnetic biological sensor may be designed to capture biomolecules attached to MNPs, which typically range from a few nanometers to less than approximately 100 nanometers (nm), and more typically on the order of 1 to 10 nm. As another example, the biological sensor may be configured to capture biomolecules attached to magnetic microbeads, which may be on the order of sub-one micron (μm) up to 2 μm (e.g., about 100 nm to about 2000 nm).

In one aspect, the disclosure describes a magnetic biosensor comprising a magnetic stack comprising a free layer, a fixed layer, and a nonmagnetic layer between the free layer and the fixed layer. At least one of the free layer or the fixed layer may have a magnetic moment oriented out of a major plane of the free layer or the fixed layer, respectively, in an absence of an external magnetic field. The magnetic biosensor also may include a sample container disposed over the magnetic stack, a plurality of capture antibodies attached to a bottom surface of the sample container above the magnetic stack, and a magnetic field generator configured to generate a magnetic field substantially perpendicular to the major plane of the free layer or fixed layer.

In another aspect, the disclosure describes a magnetic biosensor array comprising a plurality of electrodes located along at least one peripheral edge of the magnetic biosensor array, a sample container, and a plurality of magnetic biosensors each located adjacent to the sample container and comprising a magnetic stack comprising a free layer, a fixed layer, and a nonmagnetic layer between the free layer and the fixed layer. At least one of the free layer or the fixed layer may have a magnetic moment oriented out of a major plane of the free layer or the fixed layer, respectively, in an absence of an external magnetic field. The magnetic biosensor array also can include a plurality of capture antibodies attached to a bottom surface of the sample container above the plurality of magnetic biosensors.

In a further aspect, the disclosure describes a magnetic biosensing system comprising a probe array comprising a plurality of probes and a magnetic biosensor array. The magnetic biosensor array may include a plurality of electrodes located along at least one peripheral edge of the magnetic biosensor array, a sample container, and a plurality of magnetic biosensors each located adjacent to the sample container and comprising a magnetic stack comprising a free layer, a fixed layer, and a nonmagnetic layer between the free layer and the fixed layer. At least one of the free layer or the fixed layer may have a magnetic moment oriented out of a major plane of the free layer or the fixed layer, respectively, in an absence of an external magnetic field. The magnetic biosensor array also can include a plurality of capture antibodies attached to a bottom surface of the sample container above the plurality of magnetic biosensors. The plurality of electrical contacts are located along at least one edge of the sensor chip and are configured to receive respective ones of the plurality of probes. The magnetic biosensing system also can include a motor configured to move the probe array toward and away from the magnetic biosensor array to engage and disengage the plurality of probes and the plurality of electrical contacts and a magnetic field generator located below the magnetic biosensor array to apply a magnetic field in a direction perpendicular to a major plane of the magnetic biosensor array.

In an additional aspect, the disclosure describes a method for forming a magnetic biosensor. The method may include forming a magnetic stack comprising a free layer, a fixed layer, and a nonmagnetic layer between the free layer and the fixed layer. At least one of the free layer or the fixed layer may have a magnetic moment oriented out of a major plane of the free layer or the fixed layer, respectively, in an absence of an external magnetic field. The method also may include placing a sample container over the magnetic stack and attaching a plurality of capture antibodies to a bottom surface of the sample container above the magnetic stack.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIG. 1 is a schematic diagram of an example magnetic biosensing system in which the external magnetic field is oriented in-plane with respect to the free layer of the sensor.

FIGS. 2A and 2B are conceptual diagrams that illustrate an example technique by which a magnetic biosensor may detect a concentration of an analyte in a sample.

FIGS. 12A and 12B are conceptual diagrams of an example magnetic biosensor array that includes a plurality of individual magnetic biosensors without and with electrical connections to a plurality of probes, respectively.

FIGS. 12C and 12D are images of an example probe station and magnetic biosensor array with the probe station not contacting and contacting the magnetic biosensor array, respectively.

FIG. 39 is a conceptual diagram that illustrates an example configuration of a magnetic biosensor configured to detect estradiol.

DETAILED DESCRIPTION

Figures 3A, 3B:
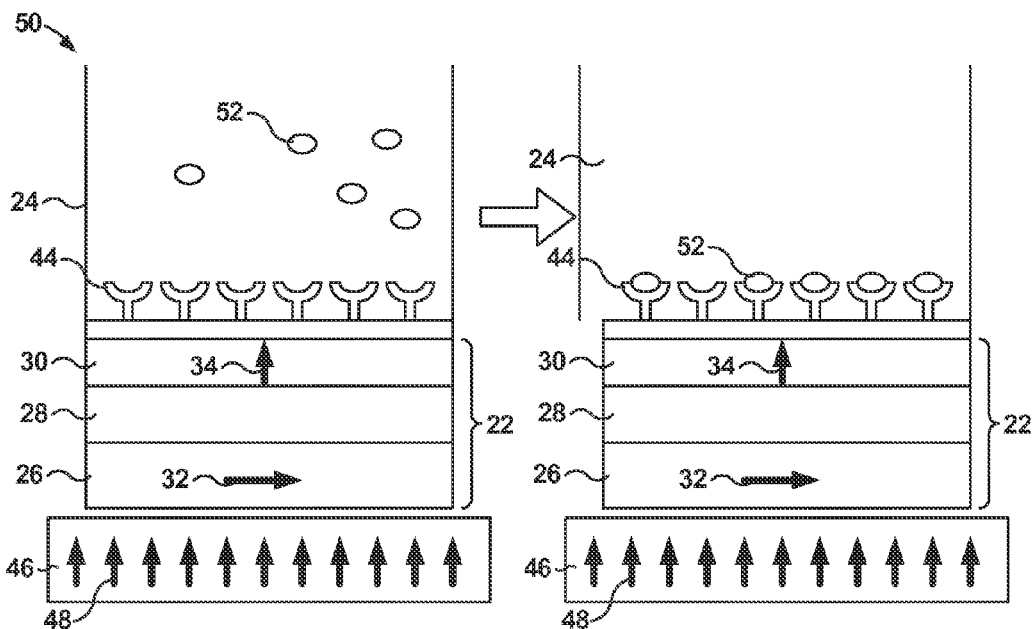
FIGS. 3A-3D are conceptual diagrams that illustrate another example technique by which a magnetic biosensor may detect a concentration of an analyte in a sample.

The disclosure describes magnetic biomolecule sensors and magnetic biomolecule sensing systems. In one or more aspects, the disclosure describes a magnetic biomolecule sensor that includes a magnetic sensor having a free layer, a fixed layer, or both, with a magnetic moment that is oriented out of a major plane of the layer in a magnetically stable state (e.g., in the absence of an external magnetic field). In some examples, the magnetic moment of the free layer, the fixed layer, or both may be oriented substantially perpendicular to the major plane of the layer in the magnetically stable state.

The out-of-plane orientation of the magnetic moment of the free layer, fixed layer, or both, may facilitate application of an external magnetic field to the magnetic sensor in a direction perpendicular to a major plane of the free layer. By applying the external magnetic field in a direction perpendicular to the major plane of the free layer, a system configured to simultaneously process a plurality of samples (e.g., tens, hundreds, or thousands of samples) may be constructed. For example, the system may include a magnetic field source, a plurality of magnetic biosensors disposed on the magnetic field source, and a sample holder for a plurality of samples disposed on the plurality of magnetic biosensors. In this configuration, a distance between the magnetic field source and each of the plurality of magnetic biosensors may be substantially the same, which may result in each of the plurality of magnetic biosensors being exposed to substantially the same applied magnetic field.

Thus, a plurality of samples may be processed in parallel by a plurality of magnetic sensors.

The sample holder can include a plurality of sample containers, each sample container configured to hold a sample. In some implementations, the sample container may be a reaction well, in which the sample is placed and stays throughout testing. In various examples, the sample container may be configured to hold small amounts of sample (e.g., nanoliters (nL) or microliters (μL)) or larger amounts of sample (e.g., milliliters (mL)). Different size sample containers may be used for different types of sample testing. For example, small volume sample holders may be used for drug discovery, while larger volume sample holders may be used for diagnostic testing.

In some implementations, the sample containers may be microfluidic channels, through which the sample flows. A series of sensors may be substantially aligned along a bottom of the microfluidic channel to detect analytes moving through the microfluidic channel. In this way the magnetic biomolecule sensors can be utilized in a variety of testing applications.

FIGS. 2A and 2B are conceptual diagrams that illustrate one technique by which a magnetic biosensor 20 may detect a concentration of an analyte in a sample. The technique illustrated conceptually in FIGS. 2A and 2B may be referred to as detection by competition. As shown in FIG. 2, magnetic biosensor 20 may include a magnetic stack 22 and a sample container 24. In the simplified example shown in FIG. 2, magnetic stack 22 includes a fixed magnetic layer 26, a nonmagnetic layer 28, and a free magnetic layer 30. In some implementations, magnetic stack 22 may include additional layers. Examples of other magnetic stacks that can be used in magnetic biosensor 20 are described below.

Fixed magnetic layer 26 includes a magnetic material formed in a manner such that a magnetic moment 32 of fixed magnetic layer 26 is substantially fixed in a selected direction under magnetic fields experienced by the fixed magnetic layer 26. As shown in FIGS. 2A and 2B, magnetic moment 32 of fixed magnetic layer 26 is fixed in an in-plane direction (i.e., a direction within a major plane of fixed magnetic layer 26). In other examples, magnetic moment 32 may be fixed in a direction out of the plane of fixed magnetic layer 26. For instance, magnetic moment 32 may be fixed at an angle canted out of the plane between about 1 degree and about 90 degrees (where 90 degrees is substantially normal to the major plane of fixed magnetic layer 26). In some implementations, magnetic moment 32 may be fixed in a direction substantially normal (perpendicular) to the major plane of fixed magnetic layer 26. In some examples, magnetic moment 32 of fixed magnetic layer 26 is fixed using one or more additional layers (not shown) in magnetic stack 22, e.g., using anti-ferromagnetic coupling.

Various magnetic materials may be used for forming fixed magnetic layer 26, including, for example, cobalt-iron-boron (CoFeB) alloys, palladium/cobalt (Pd/Co) multilayer structures, combinations thereof, or the like. Thickness of fixed magnetic layer 26 may depend on, for example, the material used to formed fixed magnetic layer 26, a thickness of nonmagnetic layer 28, a thickness of free magnetic layer 30, and other variables.

Nonmagnetic layer 28 provides spacing between fixed magnetic layer 26 and free magnetic layer 30. Nonmagnetic layer 28 may include a nonmagnetic material, such as, for example, an oxide or a dielectric material. In some examples, nonmagnetic layer 28 may include magnesium oxide (MgO). A thickness of nonmagnetic layer 28 may vary and be selected based upon, for example, properties of free magnetic layer 30 and fixed magnetic layer 26. In an example, nonmagnetic layer 28 may be formed of MgO and have a thickness of about 1.7 nm. In some examples, nonmagnetic layer 28 may be referred to as a spacer layer.

Free magnetic layer 30 includes a magnetic material formed in such a manner to allow a magnetic moment 34 of free magnetic layer 30 to rotate under influence of an external magnetic field (i.e., external to magnetic stack 22). Free magnetic layer 30 is also formed to that magnetic moment 34 of free magnetic layer 30 is oriented in a selected direction in the absence of an external magnetic field (referred to as a magnetically stable state). In the example shown in FIGS. 2A and 2B, magnetic moment 34 is formed such that a magnetically stable state is perpendicular to a major plane of free magnetic layer 30. In other examples, magnetic moment 32 may have a magnetically stable state in another direction out of the plane of free magnetic layer 30. For instance, magnetic moment 34 may have a magnetically stable state at an angle canted out of the plane between about 1 degree and about 90 degrees (where 90 degrees is substantially normal to the major plane of free magnetic layer 30). In other implementations, e.g., when magnetic moment 32 of fixed magnetic layer 26 is fixed in a direction out of the plane of fixed magnetic layer 26, magnetic moment 34 of free magnetic layer 30 may have a magnetically stable state parallel to the major plane of free magnetic layer 30.

Free magnetic layer 30 may be formed of magnetic metals or alloys, such as, for example, a CoFeB alloy. A thickness of free magnetic layer 30 may be selected based on a number of variables, including, for example, a selected sensing regime, an external field to be applied to magnetic stack 22, composition and/or thickness of fixed magnetic layer 26 and nonmagnetic layer 28, or the like. In some examples, the thickness of free magnetic layer 30 can be between about 1 nm and about 3 nm, such as about 1.1 nm, about 1.3 nm, about 1.5 nm, about 1.7 nm, or about 2 nm.

Magnetic biosensor 20 also includes a magnetic field generator 46, which may include, for example, a permanent magnetic or an electromagnet. Magnetic field generator 46 generates a substantially constant magnetic field 48 oriented in a direction perpendicular to a major plane of free layer 30. Magnetic field 48 biases magnetic moment 34 of free layer 30 in a direction substantially parallel to magnetic field 48.

Sample container 24 may be formed of any material suitable for containing a sample. For example, Sample container 24 may be formed of a polymer, plastic, or glass that is substantially nonreactive with components of the sample. In some instances, sample container 24 is a reaction well. In other examples, sample container 24 is a microfluidic channel. Sample container 24 may be any suitable shape, including, for example, a hollow cylinder, a hollow cube, an elongated channel, or the like. In some instances, sample container 24 is sized to contain a small amount of sample, e.g., nL or μL of sample. For example, sample container 24 may be sized to contain about 40 μL of sample. In other instances, sample container 24 is sized to contain larger amounts of sample, e.g., mL of sample. For example, sample container 24 can be a cylindrical well with a radius of about 25 millimeters (mm) and a height of about 2 mm, which has a volume of about 3.925 mL.

In some examples, instead of a single sample container 24 being coupled to or associated with a single magnetic stack 22 (as shown in FIGS. 2A and 2B), a single sample container 24 may be associated with or coupled to a plurality of magnetic stacks 22. For example, a single sample container 24 may be associated with or coupled to at least four sensors, such as 25 sensors or 320 sensors.

Within sample container 24 and attached, e.g., chemically bonded, to a surface of sample container 24 are a plurality of capture molecules or capture antibodies 44. Capture antibodies 44 may be selected to capture molecules of interest in the sample disposed within sample container 24. Although a single type of capture antibodies 44 is shown in FIGS. 2A and 2B, in other examples, multiple types of capture antibodies 44 (e.g., configured to capture different molecules of interest) may be attached to the surface of sample container 24, e.g., at different locations of sample container 24. In some implementations, when sample well 24 includes a plurality of different types of capture antibodies 44, each type of capture antibodies 44 may be disposed adjacent to a different magnetic stack 22. For example, a single type of capture antibodies 44 may be associated with a single magnetic stack 22, and a sample container 24 may be associated with a plurality of magnetic stacks 22.

In a detection-by-competition technique, a sample, which includes a plurality of unmarked analytes 42 or unmarked antigens 42, and a reagent, which includes a plurality of magnetically marked analytes 36, are mixed and deposited in sample container 24, as shown in FIG. 2A. Magnetically marked analytes 36 include a molecule of interest, also referred to as a magnetically marked antigen 38. Magnetically marked antigen 38 may be the same molecule as unmarked antigens 42 or may possess the same binding properties (to capture antibodies 44) as unmarked antigens 42.

Magnetically marked antigen 38 is bound to a magnetic nanoparticle (MNP) 40. MNPs 40 can include a high magnetic moment material such as FeCo, FeCoN, FeSi, FeC, FeN, combinations of Fe, N, C, Si, or the like. MNPs 40 can be fabricated using various techniques, including physical vapor nanoparticle-deposition. The size of MNPs 40 can be controlled to be in the range of, for example, 3 to 100 nm. Because the size and shape of MNPs 40 affect the magnetic properties of MNPs 40, which affects operation of magnetic stack 22, the size and shape of MNPs 40 may be controlled to be substantially uniform. In some examples, MNPs 40 may be substantially cubic in shape and substantially the same size, e.g., defined by a width of the respective one of MNPs 40.

As shown in FIG. 2B, magnetically marked antigens 38 and unmarked antigens 42 compete to bind at capture antibodies 44. Because of this, the number of magnetically marked antigens 38 bound by capture antibodies 44 is inversely proportional to the concentration of unmarked antigens 42 in the sample. The MNPs 40 generate magnetic fields, which affect the orientation of magnetic moment 34. For example, as shown in FIG. 2B, the magnetic fields generated by MNPs 40 of magnetically marked analytes 36 captured by capture antibodies 44 affects magnetic moment 34 in a downward direction of FIG. 2B. This change of magnetic moment 34 of free layer 30 changes a magnetoresistance of magnetic stack 22, which may be measured by sending applying a voltage across magnetic stack 22 and measuring the resulting current. After generating a calibration curve of measured current versus known concentration of unmarked antigens 42, the calibration curve and measured current across magnetic stack 22 may be used to determine a concentration of unmarked antigens in the sample.

FIGS. 3A-3D are conceptual diagrams that illustrate another technique by which a magnetic biosensor may detect a concentration of an analyte in a sample. The technique illustrated in FIGS. 3A-3D may be referred to as a three-layer technique or a sandwich technique.

As shown in FIGS. 3A-3D, in some implementations, magnetic biosensor 50 may be similar to magnetic biosensor 20 of FIGS. 2A and 2B, aside from the differences described herein. For example, magnetic stack 22 may be substantially similar to or the same as any of the configurations of magnetic stack 22 described with respect to FIGS. 2A and 2B or other examples described below. Similarly, sample container 24 and magnetic field generator 46 may be similar to or the same as those structures described with reference to FIGS. 2A and 2B.

The three-layer technique differs from the detection-by-competition (two-layer) technique in that a sample including analyte or antigens 52 are first deposited in sample container 24, as shown in FIG. 3A. Antigens 52 are then allowed time to bind to capture antibodies 44, as shown in FIG. 3B. Once antigens 52 have been allowed time to bind to capture antibodies 44, the sample is removed and, in some implementations, the sample container may be rinsed with a solvent to remove any sample residue.

Figures 3C, 3D:
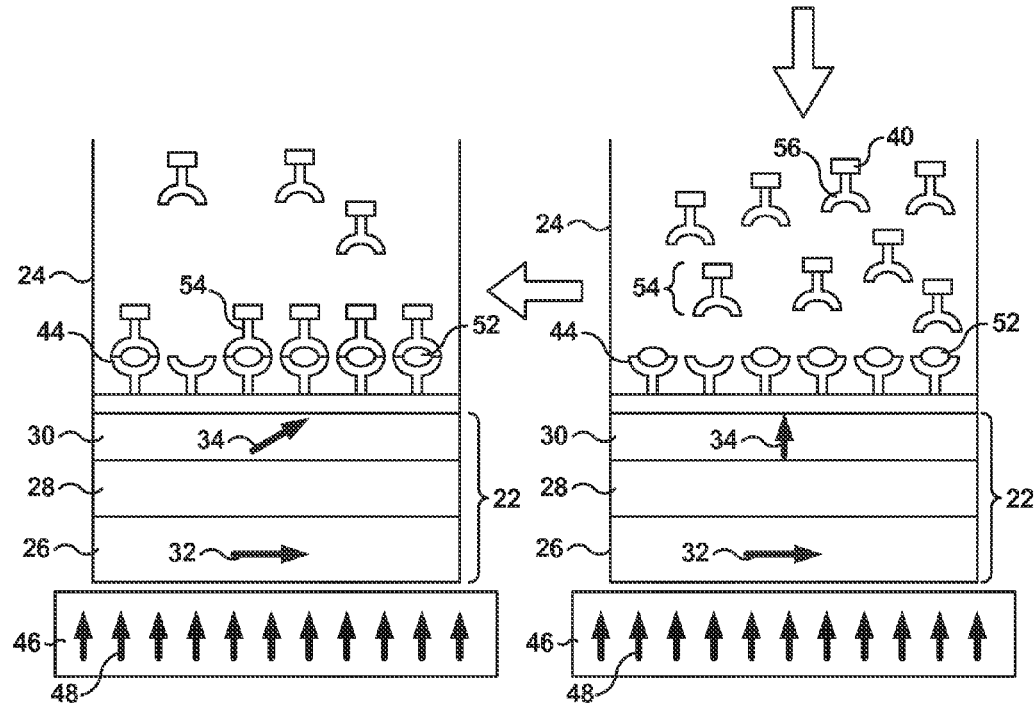

As shown in FIG. 3C, a solution containing excess magnetically labeled detection antibodies 54 is introduced into sample container 24. Each of magnetically labeled detection antibodies 54 includes a MNP 40, which may be similar to or the same as MNP 40 of FIGS. 2A and 2B, and a detection antibody 56. Detection antibody 56 is keyed to bond to antigen 52.

As shown in FIG. 3D, magnetically labeled detection antibodies 54 bond to antigens 52. After sufficient time to allow bonding, the solution and excess magnetically labeled detection antibodies 54 may be removed and a voltage applied across magnetic stack 22 to measure the resistance of magnetic stack 22. As described above, the resistance of magnetic stack is a function of the relative orientations of magnetic moment 32 of fixed layer 26 and magnetic moment 34 of free layer 30. As the orientation of magnetic moment 34 is affected by the magnetic fields generated by MNPs 40, the resistance may be change based on the number of magnetically marked detection antibodies 54 bound to antigens 52. For example, as shown in FIG. 3D, the magnetic fields generated by MNPs 40 of magnetically marked detection antibodies 52 affect magnetic moment 34 in a downward direction of FIG. 3D. This change of magnetic moment 34 of free layer 30 changes a magnetoresistance of magnetic stack 22, which may be measured by sending applying a voltage across magnetic stack 22 and measuring the resulting current. After generating a calibration curve of measured current versus known concentration of antigens 52, the calibration curve and measured current across magnetic stack 22 may be used to determine a concentration of unmarked antigens in the sample.

Magnetic biosensor 20, 50 shown in FIGS. 2A, 2B, and 3A-3D can be used to detect and quantify a concentration of various antigens. For example, magnetic biosensors 20, 50 can be used to detect antigens based on specific interactions for oligonucleotides, such as DNA-DNA or RNA-RNA interactions; small-molecule-biomolecule interactions; aptamer-biomolecule interactions; protein interactions; or the like. In this way, magnetic biosensors 20, 50 allow application of an external magnetic field perpendicular to a major plane of a magnetic stack 22 (e.g., a major plane of free layer 30). Such a configuration may facilitate substantially simultaneous or parallel testing of a plurality of samples in different sample containers using a single system.

Figure 4:
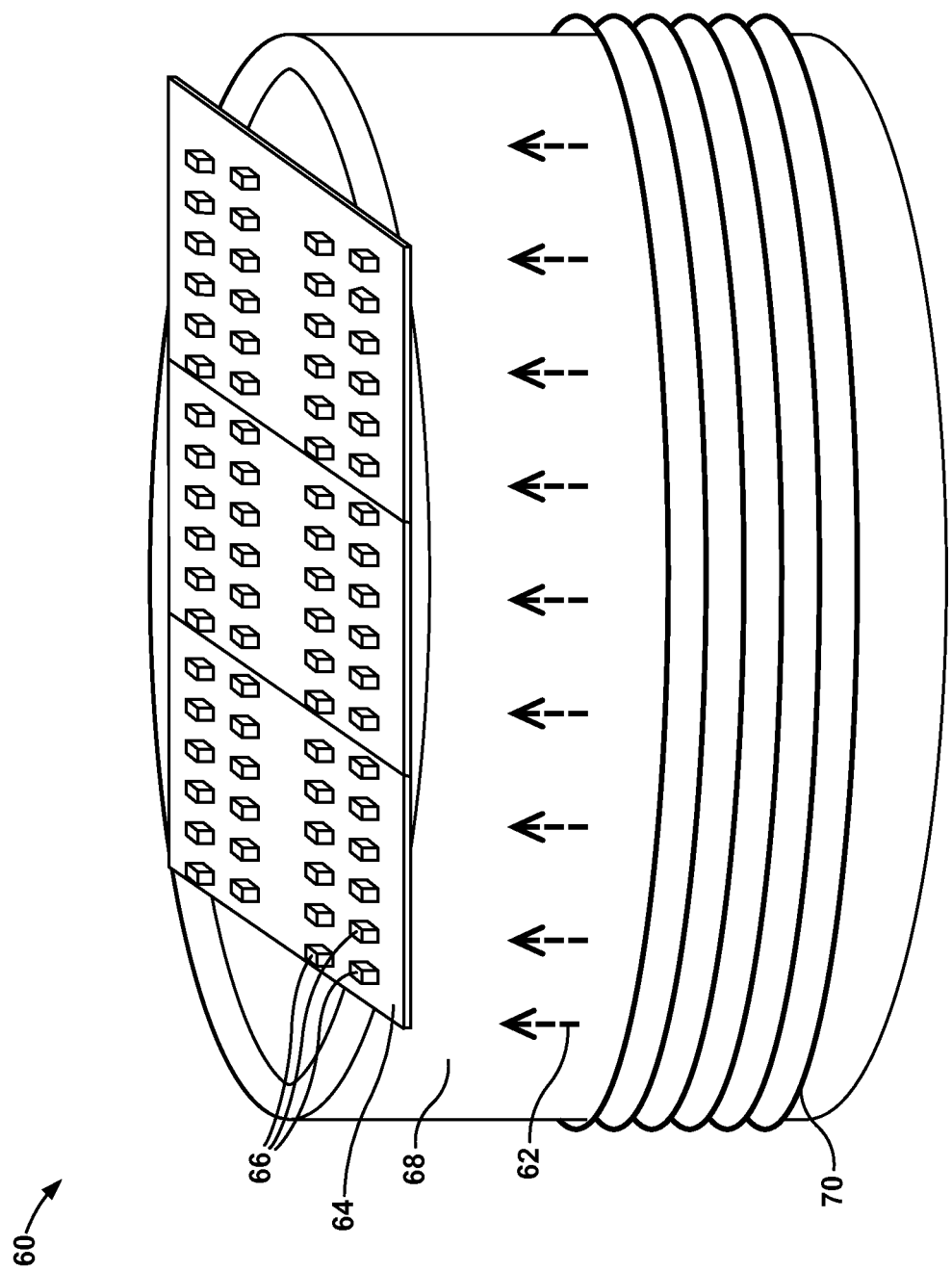
FIG. 4 is a schematic diagram of an example magnetic biosensing system in which the external magnetic field is oriented perpendicular to a major plane of the free layer of the sensor.

FIG. 4 is a schematic diagram illustrating an example magnetic biosensing system 60 in which the external magnetic field (indicated by arrows 62) is oriented substantially perpendicular to a major plane of sample plate 64. The substantially perpendicular or out-of-plane configuration may be utilized to allow testing of a large number of samples substantially simultaneously or in parallel.

As shown in FIG. 4, each sample may be contained in a respective one of magnetic biosensors 66. In some examples, each of magnetic biosensors 66 may have a configuration similar to that described and shown with reference to magnetic biosensors 20 or 50 shown in FIGS. 2A and 2B or FIGS. 3A-3D, and the configuration of each of magnetic biosensors 66 may be the same or different. Although not shown in FIG. 4, a major plane of a free layer (e.g., free layer 30 of FIGS. 2A, 2B, and 3A-3D) of the magnetic stack in each of magnetic biosensors 66 may be oriented substantially parallel to the major plane of sample plate 64. Hence, the external magnetic field (indicated by arrows 62) is oriented substantially perpendicular to the major planes of the free layers of each respective one of biosensors 66. This configuration of magnetic biosensing system 60 allows placing sample plate 64 more closely to magnetic field generator 68 (e.g., compared to the in-plane configuration shown in FIG. 1).

In the example shown in FIG. 4, magnetic field generator 68 is an electromagnetic and includes coils 70 for generating the magnetic field. In other examples, magnetic field generator 68 can be another type of magnetic field generator, such as a permanent magnet. The design also can provide a large (e.g., about 800 Oe) out-of-plane magnetic field that is substantially uniform over the surface of magnetic field generator 68. Using this configuration of magnetic biosensing system 60, a bench top type biomedical detection system can be built which can test, for example, more than tens, hundreds, or thousands of samples substantially simultaneously or within a short time period, such as within about 5 minutes. Also, in some implementations, magnetic biosensing system 60 may allow the automatic handling and testing of samples, e.g., by a computer-controlled robotic system.

Figure 5C:
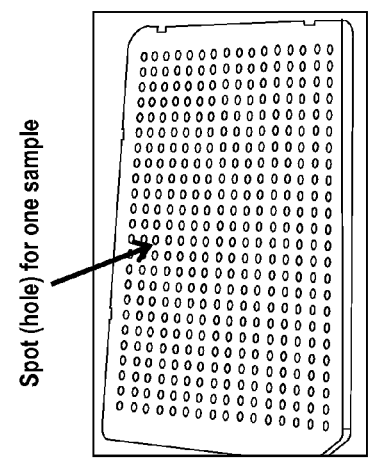
FIGS. 5A-5D are images of examples of a magnetic biosensing system having a perpendicular applied magnetic field for parallel testing of a plurality of samples.
Figure 5D:
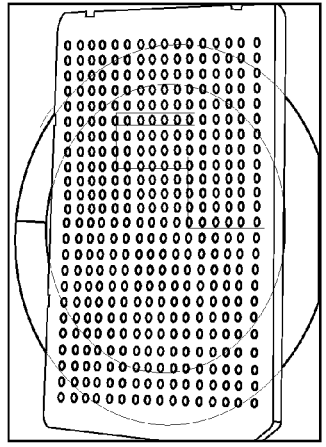
Figure 5B:
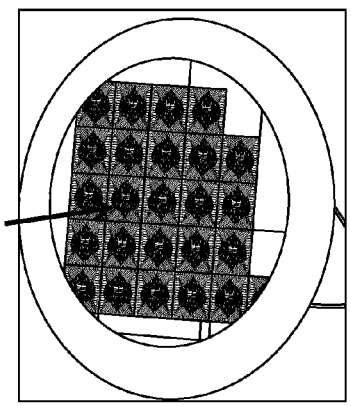
Figure 5A:
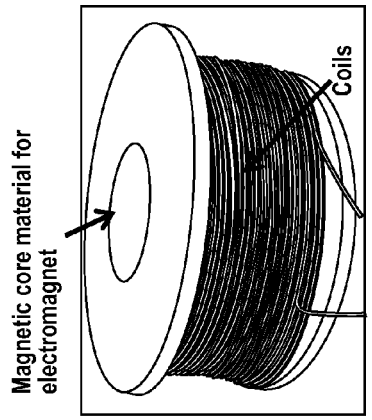

FIGS. 5A-5D are images of examples of a magnetic biosensing system having a perpendicular applied magnetic field for parallel testing of a plurality of samples. FIG. 5A shows an electromagnet assembly (a magnetic field generator) that is compatible with a bench top setup and can provide a substantially uniform magnetic field of greater than 500 Oe over a substantial portion of a top of the electromagnet assembly. As shown in FIG. 5B, the electromagnet assembly is sized to be capable of holding 1600 magnetic biosensors spread among 24 separate chips. In some examples, the magnetic biosensors shown in FIG. 5B may have the same or a similar configuration as magnetic biosensor 20 or magnetic bionsensor 50. FIG. 5C shows a sample holder disposed on the magnetic biosensors with 384 individual reaction wells (e.g., sample containers). Each reaction well can hold one sample. FIG. 5D shows the magnetic biosensing system fully assembled. The sample holder is placed on the top of the magnetic biosensors, which are laid on the magnet assembly. This configuration may allow a large number of samples to be tested substantially simultaneously.

As described above, to facilitate using an out-of-plane magnetic field with magnetic biosensors 66, a magnetic stack of the biosensors 66 may include a free layer, a fixed layer, or both that has out-of-plane magnetic anisotropy (e.g., an out-of-plane magnetic moment in a magnetically stable state). Two example configurations for the stacked layer materials with out-of-plane anisotropy are described with respect to FIGS. 6 and 7.

Figure 6:
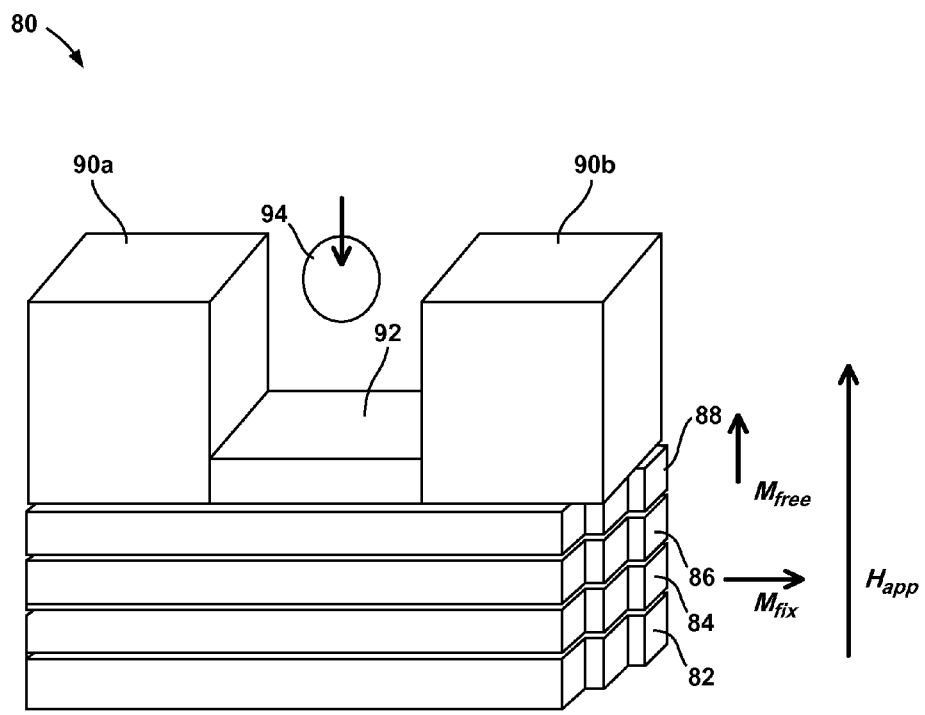
FIG. 6 is a conceptual diagram of a magnetic biosensor with in-plane magnetic anisotropy in the fixed layer and out-of-plane magnetic anisotropy in the free layer.

FIG. 6 is a conceptual diagram of a magnetic biosensor 80 with in-plane magnetic anisotropy in the fixed layer 84 and out-of-plane magnetic anisotropy in the free layer 88. Magnetic biosensor 80 includes a substrate 82, which may include, for example, glass, silicon, or another nonmagnetic material. Formed on substrate 82 is fixed layer 84, which may be similar or the same in materials and thickness to fixed layer 26 of FIGS. 2A, 2B, and 3A-3D. Fixed layer 84 has in-plane magnetic anisotropy, which means that a magnetic moment of fixed layer 84 is fixed in an in-plane direction. Nonmagnetic layer 84 is formed on fixed layer 82 and may be similar or the same in materials and thickness to nonmagnetic layer 28 of FIGS. 2A, 2B, and 3A-3D. Free layer 88 is formed on nonmagnetic layer 86 and may be similar or the same in materials and thickness to free layer 30 of FIGS. 2A, 2B, and 3A-3D. Free layer 88 has in-plane magnetic anisotropy, which means that a magnetic moment of free layer 88 has stable states in antiparallel directions out-of-the-plane of free layer 88. As described above, in some examples, free layer 88 may have magnetically stable states substantially perpendicular to a major plane of free layer 88 or may have magnetically stable states canted out of the major plane of free layer 88 at any angle greater than zero degrees.

Formed on top of free layer 30 are a first electrical lead 90a and a second electrical lead 90b (collectively, "electrical leads 90"). A $SiO_2$ insulator layer 92 is formed between electrical leads 90. Electrical leads 90 are used for applying a voltage across the magnetic stack of magnetic biosensor 80, which is used to detect the resistance of the magnetic stack. As described above, the resistance of the magnetic stack depends on the relative orientation of the magnetic moments of fixed layer 84 and free layer 88. The magnetic moment of free layer 88 rotates under an applied field (such as applied magnetic field, $H_{app}$) or a magnetic field generated by a magnetic label 94. Operation of magnetic biosensor 80 may be similar or the same as magnetic biosensors 20 and 50 from FIGS. 2A, 2B, and 3A-3D.

Figure 7:
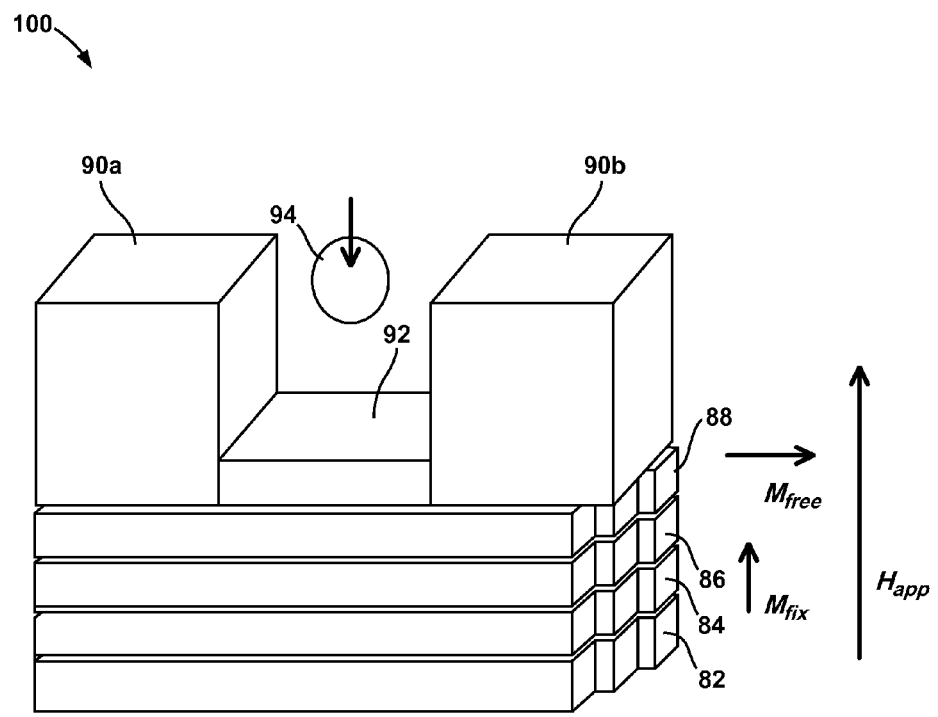
FIG. 7 is a conceptual diagram of a magnetic biosensor with out-of-plane magnetic anisotropy in the fixed layer and in-plane magnetic anisotropy in the free layer.

FIG. 7 is a conceptual diagram of a magnetic biosensor 100 with out-of-plane magnetic anisotropy in the fixed layer 84 and in-plane magnetic anisotropy in the free layer 88. Magnetic biosensor 100 is substantially similar to magnetic biosensor 80 of FIG. 6, apart from the differences in magnetic anisotropy of fixed layer 84 and free layer 88.

Figure 8:
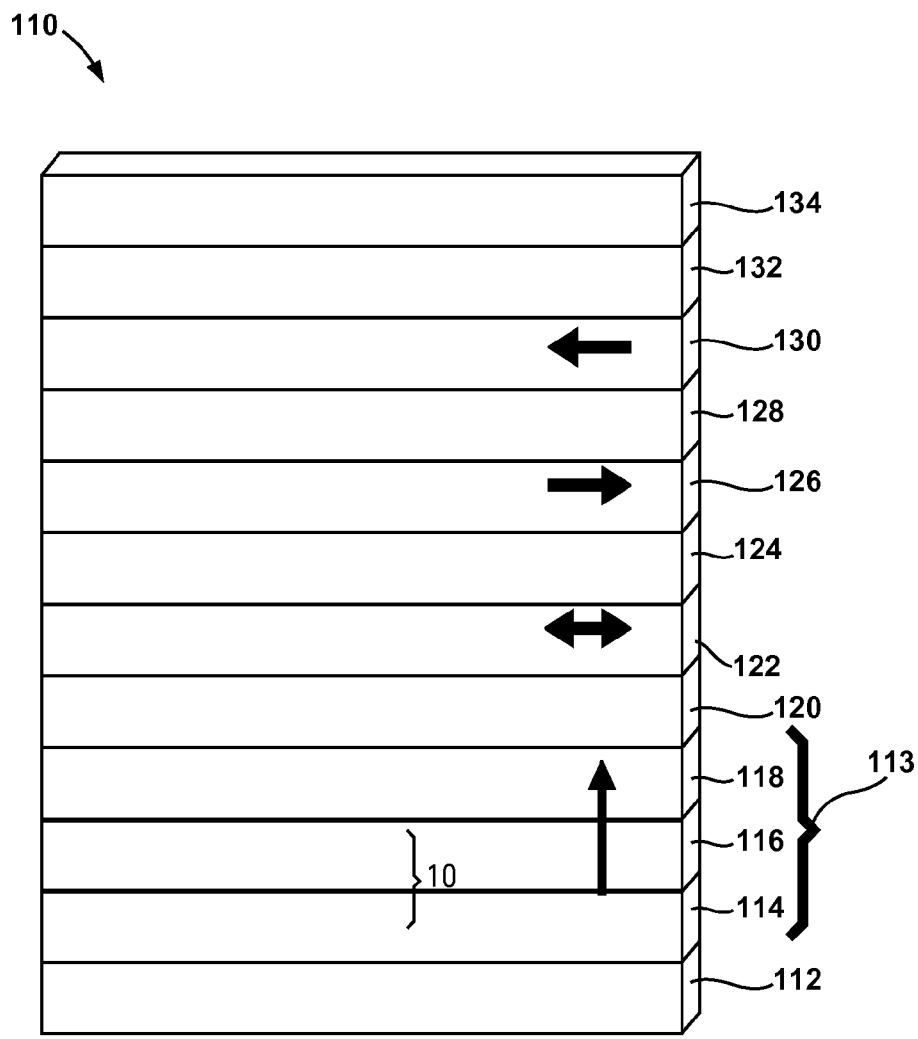
FIG. 8 is a schematic drawing of the stacked layer materials for an example magnetic tunnel junction (MTJ) structure with in-plane magnetic anisotropy in the free layer and out of plane magnetic anisotropy in the fixed layer.

FIG. 8 is a schematic diagram of the stacked layer materials for an example magnetic tunnel junction (MTJ) sensor with in-plane magnetic anisotropy in the free layer and out-of-plane magnetic anisotropy in the fixed layer, similar to FIG. 7. MTJ sensor 110 may include substrate and underlayer 112. Underlayer 112 may include a material that sets a crystal lattice for formation of the cobalt/palladium alternating layers. Fixed layer 113 includes 10 layer pairs of cobalt (Co) 114 and palladium (Pd) 116. Fixed layer 113 also includes a CoFeB layer 118 formed on the top Pd layer 116. In the example shown in FIG. 8, fixed layer 113 has a magnetic moment fixed in a direction out of a major plane of fixed layer 113, e.g., perpendicular to the plane of fixed layer 113. Formed on fixed layer 113 (i.e., CoFeB layer 118) is a first magnesium oxide (MgO) nonmagnetic layer 120. A CoFeB free layer 122 is formed on first nonmagnetic layer 120. CoFeB free layer 122 has a magnetic moment that is oriented in-plane in the absence of an external magnetic field. A second MgO nonmagnetic layer 124 is formed on CoFeB free layer 122. On top of second MgO nonmagnetic layer 124 is formed a third CoFeB layer 126, which is antiferromagnetically coupled to a CoFe layer 130 by a ruthenium (Ru) layer 128. The antiferromagnetic coupling of CoFe layer 130 and third CoFeB layer 126 may fix the magnetic moment of third CoFeB layer 126 in a selected orientation, such as in the plane of third CoFeB layer 126, as shown in FIG. 8. A PtMn electrode layer 132 is formed on CoFe layer 130, and a cap layer 134 is formed on PtMn electrode layer 132. When being formed, this structure may be annealed at about 300° C. for about 1 hour. In some implementations, a circular MTJ device with a 60 nm diameter may be fabricated by electron beam lithography.

Figure 9:
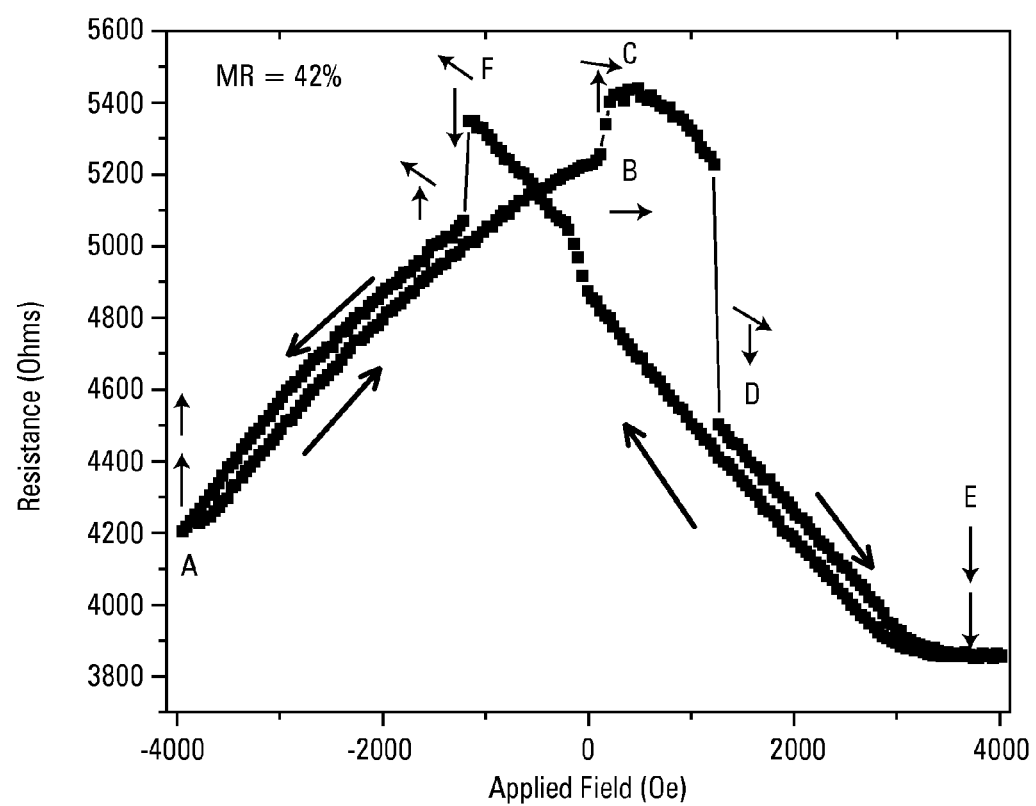
FIG. 9 is a diagram of an example magnetoresistance versus applied magnetic field curve for a circular magnetic tunnel junction (MTJ) device with about a 60 nm diameter in response to an out-of-plane applied magnetic field.

FIG. 9 is a diagram of an example magnetoresistance versus applied magnetic field curve for a circular MTJ device with a 60 nm diameter under an out-of-plane applied magnetic field. The MTJ device had a structural configuration similar to that shown in FIG. 8, with fixed magnetic layer 113 having a magnetic moment fixed out-of-the-plane and CoFeB free layer having a magnetic moment that is oriented in-plane in the absence of an external magnetic field. At point "A," magnetic moments in both the free and fixed layers are oriented out-of-plane, parallel to the applied magnetic field, and the resistance of the MTJ device is at a local minimum. Magnetoresistance of the MTJ device increases substantially linearly with decreasing negative field due to the rotation of the magnetic moment of the CoFeB free layer from perpendicular to the plane into the plane. At point "B," the magnetic moment of the CoFeB free layer is rotated completely in the plane due to the removal of the applied magnetic field (zero applied field). As shown at point "C," increasing the magnetic field in the positive direction initially causes the magnetoresistance of the MTJ device to continue to increase until a sudden drop in the magnetoresistance at around 1100 Oe (around point "D"). At this point, the magnetic moment of the Co/Pd layer reverses. Ideally, if the moments in two layers are perfectly perpendicular to each other, the reversal should not change the resistance. The small jump in the resistance is because the magnetization of the CoFeB free layer is already slightly out of the plane under this field. Further increasing the magnetic field in the positive direction to about 4,000 Oe saturates both the magnetization and the resistance. At point "E," the magnetic moments in both the CoFeB free layer and the fixed layer are completely parallel and the MTJ device reaches a local minimum magnetoresistance again.

The portions of the resistance-applied field loop from point "A" to point "B" and in the opposite direction from point "E" to point "F" are linear under an out-of-plane applied field and may be used for a magnetic biosensor. However, the applied field range for the linear portion of the loop is quite large. The range of applied fields for which the magnetic biosensor exhibits substantially linear changes in resistance can be selected by modifying parameters of the magnetic stack, such as by replacing the Co/Pd alternating layers in the fixed layer with other out-of-plane magnetic materials with lower anisotropy fields, e.g., CoFeB or Heusler alloys ($Co_2FeAl$).

To enable the high-throughput testing, e.g., of multiple samples substantially simultaneously or in a relatively short period of time, using the magnetic biosensor configuration described herein, an apparatus is needed that can quickly and reliably connect an electronic signal from the biosensor arrays to testing instrumentation. A multi-probe stage is one technique for implementing the arrangement.

Figure 10A:
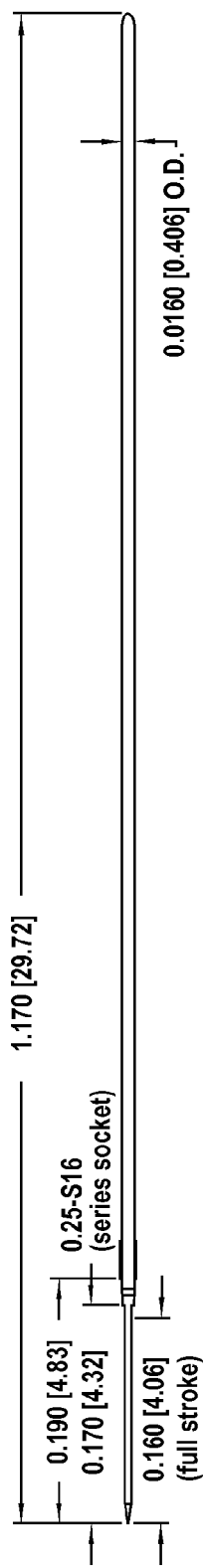
FIGS. 10A and 10B are a schematic diagram of an example probe and an image of an example probe array, respectively.
Figure 10B:
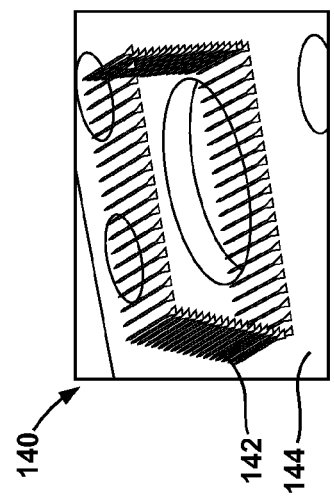

FIGS. 10A and 10B are a schematic diagram and an image of an example probe array and probe, respectively. FIG. 10A depicts example measurements of various portions of the probe. The probe may be used as an electrical contact to conductive pads of surrounding a magnetic biosensor, e.g., for electrical communication between the magnetic biosensor and an electrical system for measuring resistance of the magnetic biosensor. The first measurement shown in FIG. 10A is in inches and second measurement is in millimeters.

FIG. 10B illustrates an example probe array 140 that includes a plurality of probes 142. The probes may be used for making electrical contact with a corresponding number of contact pads on a substrate that includes a plurality of magnetic biosensors. The probes are attached to a mounting plate 144, which fixes the probes in position relative to each other. The probes 142 include a socket (not shown in FIG. 10B) for attaching to mounting plate 144. In some instances, the sockets of probes 142 are sufficiently small to realize multi-pin connection on a substrate including a plurality of magnetic biosensors. Because the electrode on the substrate can have dimensions as small as about 0.7 mm by about 0.4 mm, the connection requires a small diameter of the socket. The largest diameter of the socket is the press ring (not shown in FIG. 10B), which is at the top of the socket. The outer diameter of the press ring is about 0.022 inch (about 0.5588 mm) which can leave enough space between adjacent pins. In some examples, the length of each probe is about 1.170 inch (about 29.72 mm), which can save space for a diagnostic bench-top system.

The rated spring force for this each probe 124 is 1.6 ounces (45 g) at a 0.107" (2.7 mm) stroke. The spring may be rated for 1,000,000 cycles at ⅔ stroke (0.107 inch). The full stroke is about 0.160 inch (about 4.06 mm).

Figure 11A:
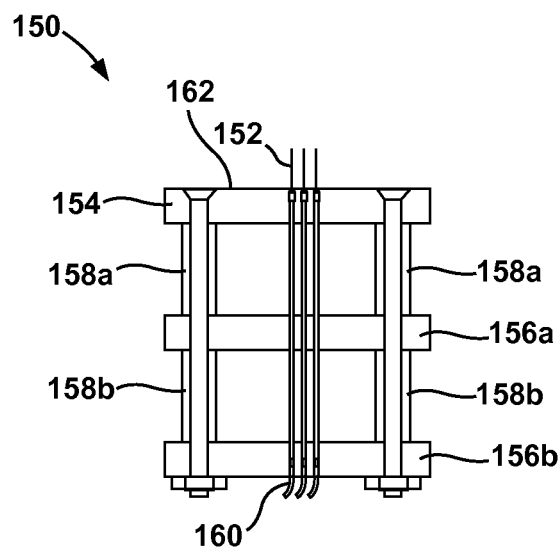
FIGS. 11A and 11B are schematic diagrams of an example triple layer station for fixing probes in place relative to each other and an example tip style for one of the probes, respectively.
Figure 11B:
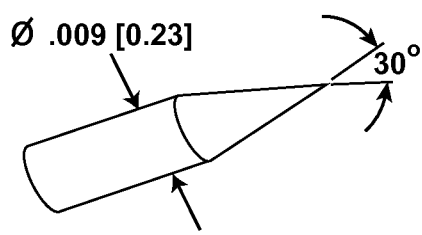

FIGS. 11A and 11B are schematic diagrams of an example triple layer station for fixing probes in place relative to each other and an example tip style for one of the probes, respectively. Triple layer station 150 may facilitate the straight and parallel alignment of all probes 152. Triple layer station 150 includes a mounting plate 154 to which probes 152 are mounted using a press ring 162. Triple layer station also includes a first guide plate 156*a* and a second guide plate 156*b*. Mounting plate 154 and first guide plate 156*a* are separated by a first set of spacers 158*a*. First guide plate 156*a* and second guide plate 156*b* are separated by a second set of spacers 158*b*. Each of probes 152 is also electrically connected to a lead wire 160, which may electrically connect to a voltage source. In some instances, alignment of probes 152 using triple layer station 150 may facilitate application of a uniform force on each of probes 152 (e.g., when contacting probes to electrical contacts of a substrate including a plurality of magnetic biosensors.

In many situations in which triple layer station 150 may be used, such as on-site water environmental testing, the surfaces of the electrical contacts may be less than ideal. The shape of spear in FIG. 11B may provide improved contact on contaminated electrical contacts due to the relatively sharp tip.

FIGS. 12A and 12B are conceptual diagrams of an example magnetic biosensor array that includes a plurality of individual magnetic biosensors without and with electrical connections to a plurality of probes, respectively. One possible layout for a magnetic biosensor array 170 could have 64 sensors disposed in sensor region 172 and 66 electrodes 174 (that may include two bus lines) in one die (chip or substrate). In some examples, where the extra electrodes (e.g., electrodes 174 in excess of the sensors) can be used for energizing, controlling, or grounding magnetic biosensor 170. In some implementations, magnetic biosensor array 170 measures about 16 mm by 16 mm. Electrodes 174 may be located along the peripheral edge of magnetic biosensor array 170. Each of electrodes 174 along the periphery may be connected to a sensor in sensor region 172, which may be located in a centrally located region of magnetic biosensor array 170. Through this contact, electrodes 174 may become energized and may communicate signals to and from each of the sensors. For example, sensed levels may be transferred to respective electrodes 174 from the sensors within the biological sampling wells, where the signals provides an indication of the number of magnetic labels biologically bonded to the sensing chip, such as on the biosensor located within each sensing well. This data is then communicated back to a computing device via probes, which are coupled to a controller, so that a user can access the data.

Figure 13:
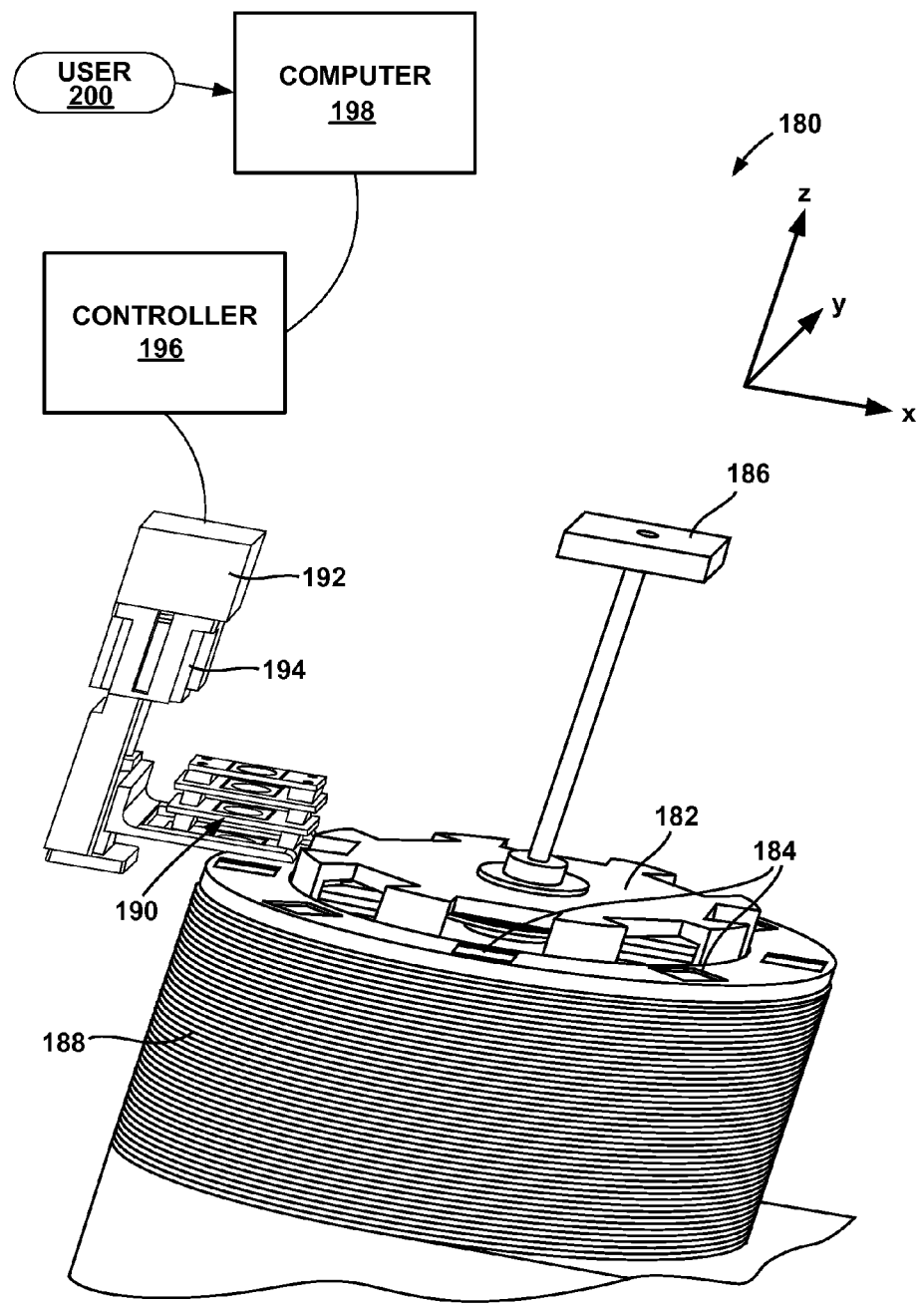
FIG. 13 is a conceptual diagram of an example magnetic biosensor system that includes a rotating sample holder and a movable probe device.

FIG. 12B illustrates a schematic diagram of an example in which a plurality of probes 176 have been brought into contact with corresponding electrodes 174. As shown in FIG. 12B, the probe arrangement may include probes 176 located in a similar arrangement as the arrangement of electrodes 170 on magnetic biosensor array 170, so each of probes 176 comes into contact with a corresponding one of electrodes 174. This contact between probes 176 and electrodes 174 may be a gateway between an external instrumentation device and sensors of magnetic bionsensor array 170, where biosampling occurs. Each of electrode 174 is configured to receive a corresponding probe 176 when, for example, the linear actuator arm lowers, lowering the probe arrangement in contact with each of electrode 174, e.g., as shown in the images of FIGS. 10C and 10D. In examples in which a spin table is utilized (e.g., as shown in FIG. 13), the spin table rotates so that each probe arrangement lowers onto a magnetic bionsensor array 170. Once the electrodes 174 of magnetic bionsensor array 170 receive the corresponding probes 176 in the probe arrangement, data transfer and energizing of that magnetic bionsensor array 170 may begin.

FIGS. 12C and 12D are photos of an example probe station and magnetic biosensor array, with the probe station not contacting and contacting the magnetic biosensor array, respectively. FIGS. 12C and 12D illustrate how a connection between the probe station and the magnetic biosensor array may be made and the process of probe station movement and contact between the individual probes and the individual electrodes.

FIG. 13 is a conceptual diagram of an example magnetic biosensor system 180 that includes a rotating sample holder and a movable probe assembly. Specifically, FIG. 13 illustrates use of a spin table 182 to test GMR and/or MTJ magnetic biosensor arrays 184. As shown, multiple samples could lie on spin table 182. The angle and speed of spin motion of spin table 182 is controlled by the stepper motor 186. A large coil 188 may be located underneath the spin table that generates a magnetic field which is perpendicular to the plane of spin table 182. By leaving the thin air gap between spin table 182 and coil 188, spin table 182 could rotate more easily and the magnetic field at the plane of magnetic biosensors 184 may still be sufficiently large and substantially vertical. The z-axis motion (where orthogonal x-y-z axes are shown in FIG. 13 for ease of description only) of probe station 190 is precisely controlled by another probe station stepper motor 192 and linear actuator 194 via a controller 196. Computer 198, which may be, for example, either a desktop, laptop, mobile computing device, or digital signal processor (DSP), may interact within controller 196 to control stepper motors 186 and 192. When a new sample has been rotated under probe station 190, linear actuator 194, under power of stepper motor 192, will lower probe station 190 to make connection with magnetic biosensor arrays 184. After finishing one test, controller 196 sends a signal to stepper motor 192 and linear actuator 194 to lift probe station 190 and to stepper motor 186 to rotate spin table 182 to position the next one of magnetic biosensor arrays 184 under probe station 190 and repeat testing. Computer 198 may execute an algorithm or control software to control magnetic biosensor system 180 to run multiple tests (e.g., tests of multiple samples and/or multiple magnetic biosensor arrays 184) in one process, automatically.

Magnetic biosensing system 180 is controlled by a user 200, who can input data into a user interface of computer 198. Computer 198 outputs signals or commands to controller 196, which outputs signals to control the movement of the stepper motors 186, 192 and/or linear actuator 194. The data transferred by computer 198 to controller 196 may additionally or alternatively relate to control aspects of sampling or sampling parameters. Once sampling is conducted by magnetic biosensing system 180, the data collected from the magnetic biosensor arrays 184 located on spin table 182 or a sample platform may be sent to controller 196 from the magnetic biosensor arrays 184, e.g., via probes coupled to probe station 190. Controller 196 then sends the data to computer 198, making it accessible to user 200 and/or computer 198 for analysis.

One or processors can be employed within computer 198, controller 196, and/or spin table 182 to control transfer the data and the magnetic biosensing system 180, including spin table 182.

In some examples, the electromagnet, including coil 188, can be replaced by a permanent magnet. In some implementations, instead of or in addition to spin table 182 being rotatable, the permanent magnetic or an electromagnetic may be movable to move underneath respective ones of magnetic biosensor arrays 184, e.g., under control of computer 198, controller 196, and/or stepper motor 186.

Figure 14:
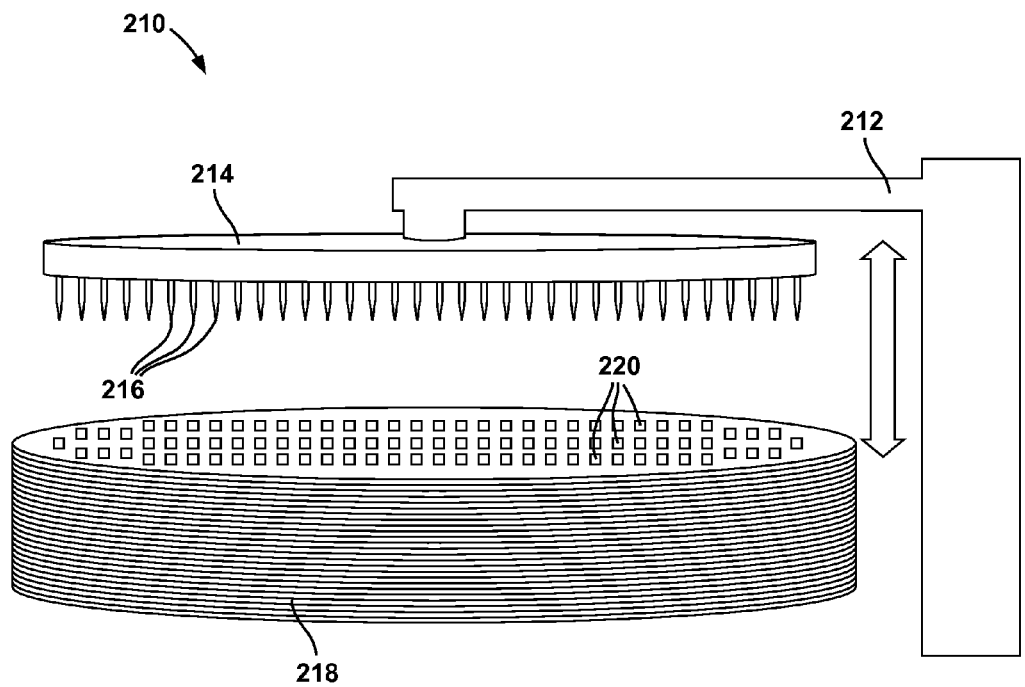
FIG. 14 is a conceptual diagram of an example high-throughput magnetic biosensor system.

FIG. 14 is a conceptual diagram of an example high-throughput magnetic biosensing system 210. To enable testing of a large number of samples simultaneously, based on the probe-station concept for magnetic biosensor array testing, a high-throughput system may be used. As an example, high-throughput magnetic biosensor system 210 can include a magnetic field generator 218, which may be an electromagnet or a permanent magnet. Disposed on magnetic field generator 218 may be a plurality of magnetic biosensors or a plurality of magnetic biosensor arrays 220. System 210 also can include a probe station 214, to which a plurality of probes 216 are attached. Probe station 214 is attached to a linear actuator 212, which is configured to move probe station 214 vertically to move the plurality of probes 216 into and out of contact with electrical contacts of magnetic biosensor arrays 220. In some examples, 25 magnetic biosensor arrays 220 may be disposed on the top plane of magnetic field generator 218. Each of magnetic biosensor arrays 220 may include, for example, 66 electrical contacts. Hence, 1650 (25 times 66) probes 216 may be attached to probe station 214, and linear actuator 212 can drive probe station 214 up and down to realize connection and disconnection between electrical contacts of magnetic biosensor arrays 220 and probes 216. Because only probe station 214 moves (and not magnetic biosensor arrays 220), magnetic biosensing system 210 system may be more stable (e.g., compared to magnetic biosensing system 180) and repetition of tests may be possible. Thus, it may be possible and efficient to test, for example, 25 samples at substantially the same time, and a bigger system with larger capacity may also be feasible by applying the same principle with additional magnetic biosensor arrays 220 and probes 216.

Figure 15:
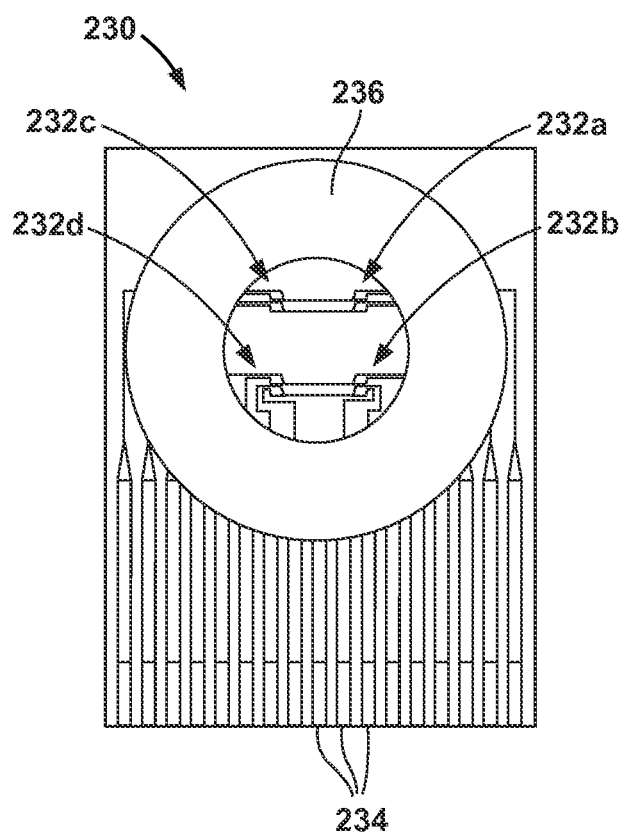
FIG. 15 is a schematic diagram of an example magnetic biosensor array configured to be clamped between magnetic field generators.

FIG. 15 is a schematic diagram of a magnetic biosensor array configured to be clamped between magnetic field generators. Magnetic biosensor array 230 includes sample (or reaction) well 236 and an array of four magnetic biosensors in each of four magnetic biosensor clusters 232a-232d disposed within sample well 236, e.g., at a bottom surface of well 236. Each of magnetic biosensor clusters 232a-232d may include four magnetic biosensors. A size of each of magnetic biosensor clusters 232a-232d may be on a scale of about 1.6 mm by about 1.6 mm, in some examples. In some instances, the distance between adjacent ones of magnetic biosensor clusters 232a-232d may be, for example, about 3.5 mm, measured from center to center. The individual magnetic biosensors (e.g., within clusters 232a-232d) may be of selected size, so that the sensor is sufficiently small so that multiple sensors may be used and output of the sensor may be sufficient for testing purposes. For example, the total area of each sensor could be about 100 µm by about 100 µm.

The arrangement of magnetic biosensor array 230 also may be substantially uniform. For example, the spacing between the sensors within a cluster (e.g., within cluster 232a) may be about 0.5 mm, measured, for example, from center to center. As shown in FIG. 15, each sensor is coupled to a respective one or more of pins 234, which provide for electrical connection between the sensors an control circuitry external to magnetic biosensor array 230. In some examples, each of pins 234 is about 3.3 mm long and about 0.5 mm in diameter and the pins are spaced apart a distance (measured, for example, from center to center) of about 1 mm. In some implementations, magnetic biosensor array 230 may have a width of about 17.3 mm and a length of about 26 mm, although a size of magnetic biosensor array 230 may be different in other examples.

Figure 16A:
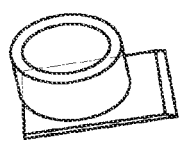
FIGS. 16A-16F are images of an example multiplex magnetic biosensor system that includes magnetic field sources clamped above and below the magnetic biosensor array.
Figure 16F:
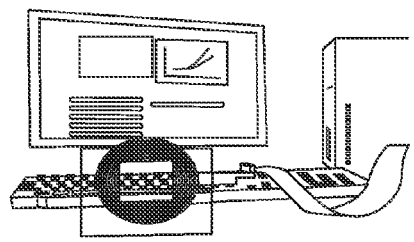
Figure 16B:
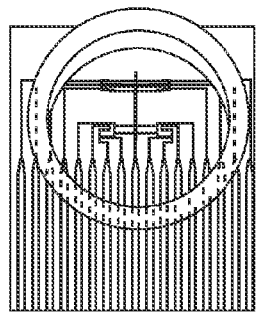
Figure 16E:
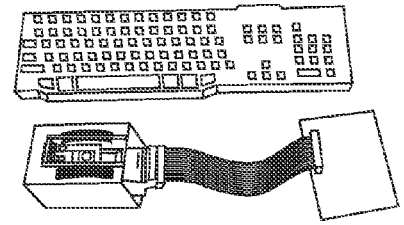
Figure 16C:
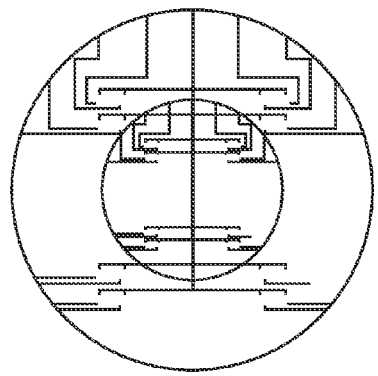
Figure 16D:
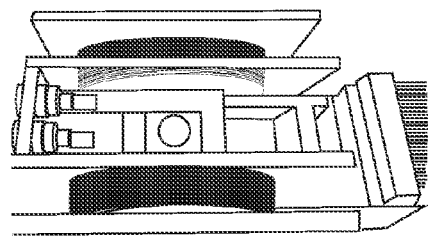

FIGS. 16A-16F are images of an example multiplex magnetic biosensor system that includes magnetic field generators clamped above and below the magnetic biosensor array. FIG. 16A shows a magnetic biosensor array with an attached reaction well. FIG. 16B is a top view of a magnetic biosensor array with an attached reaction well, and show electrical traces connected to individual magnetic biosensors and electrical pins for connecting the magnetic biosensors to external control circuitry. FIG. 16C is a zoomed-in image of four magnetic biosensors. The lighter lines are the Au electrodes and connections. FIG. 16D illustrates a magnetic biosensor array assembled in the detection system with magnetic field generators clamped on either side of the magnetic biosensor array. FIG. 16D also illustrates clamping electronic connections, where a controller and sensor chips are configured to communicate via the plurality of probe arrangements when the electrodes of the sensor chips are coupled to the probe arrangement through a clamping mechanism. FIG. 16E is an image of an example magnetic biosensing system and its connection to a signal processing chip and controller (e.g., a computer). FIG. 16F is an image of the magnetic biosensing system electrically connected to a computer executing control software, such as LabVIEW (a system design software available from National Instruments Corp., Austin, Tex.).

Figure 17:
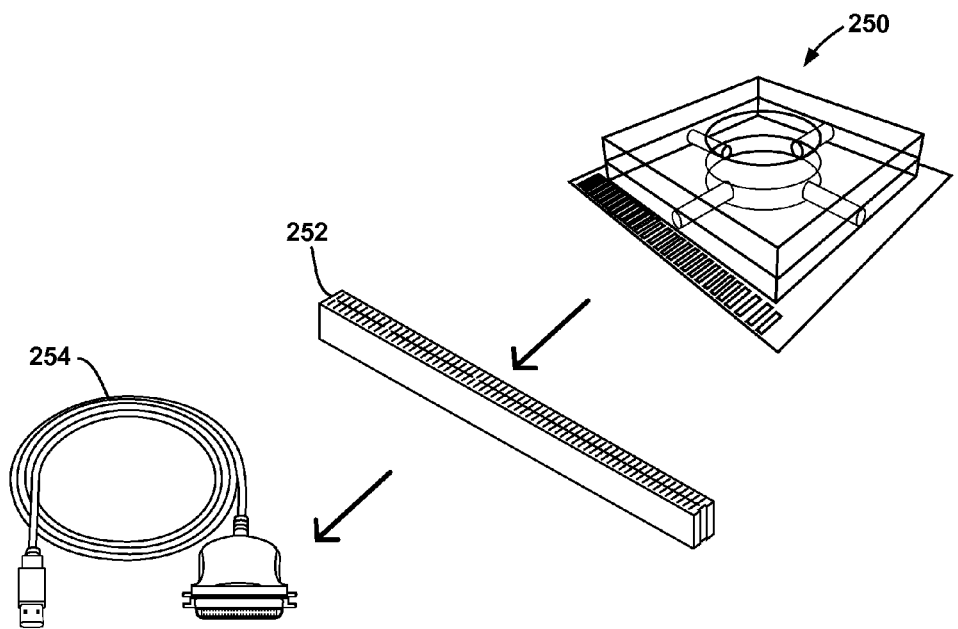
FIG. 17 is a schematic diagram of an example magnetic biosensor system.

FIG. 17 is a schematic diagram of an example magnetic biosensor system. In this example, magnetic biosensor system 250 may plug directly into a chip reader 252. In some implementations, magnetic biosensor system 250 may have a configuration similar to or substantially the same as magnetic biosensor array 230 shown in FIG. 15. Chip reader 252 may include electrically conductive contacts configured to receive pins 254 of magnetic biosensor system 250, creating a contact for communication between magnetic biosensor system 250 and chip reader 252, for example for date transfer to and from magnetic biosensor system 250 and to energize magnetic biosensor system 250. A connector, such as a universal serial bus (USB) connector 254 may be used to connect chip reader 252 to a computing device, such as a computer, to transfer the data. Chip reader 252 may also communicate with a computing device using wireless telemetry techniques.

Figure 18:
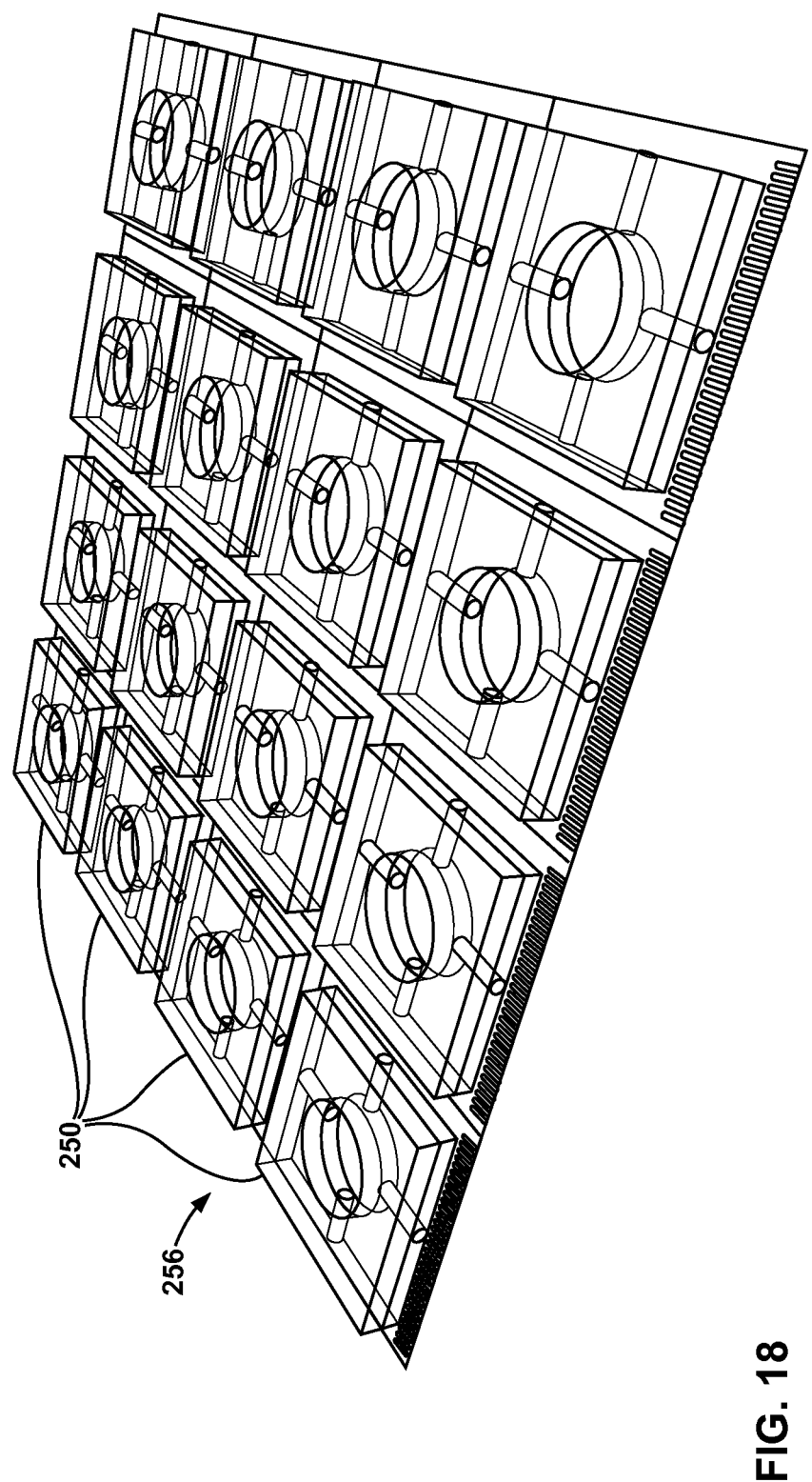
FIG. 18 is a schematic diagram of example of multiple magnetic biosensor systems connected in a platform.

In some examples, magnetic biosensor system 250 may be configured to allow connection of multiple magnetic biosensor systems 250 to each other. FIG. 18 is a schematic diagram of an example of multiple magnetic biosensor systems 250 connected on a platform 256. This arrangement of magnetic biosensor systems 250 is an example of how multiple magnetic biosensor systems 250 could be arranged on a platform 256, so that sampling of each chip could happen substantially simultaneously on one platform. Such an arrangement could be used in an ultra high-throughput system, such as described with respect to in FIG. 14, where magnetic biosensor systems 250 may also be employed.

Figure 19:
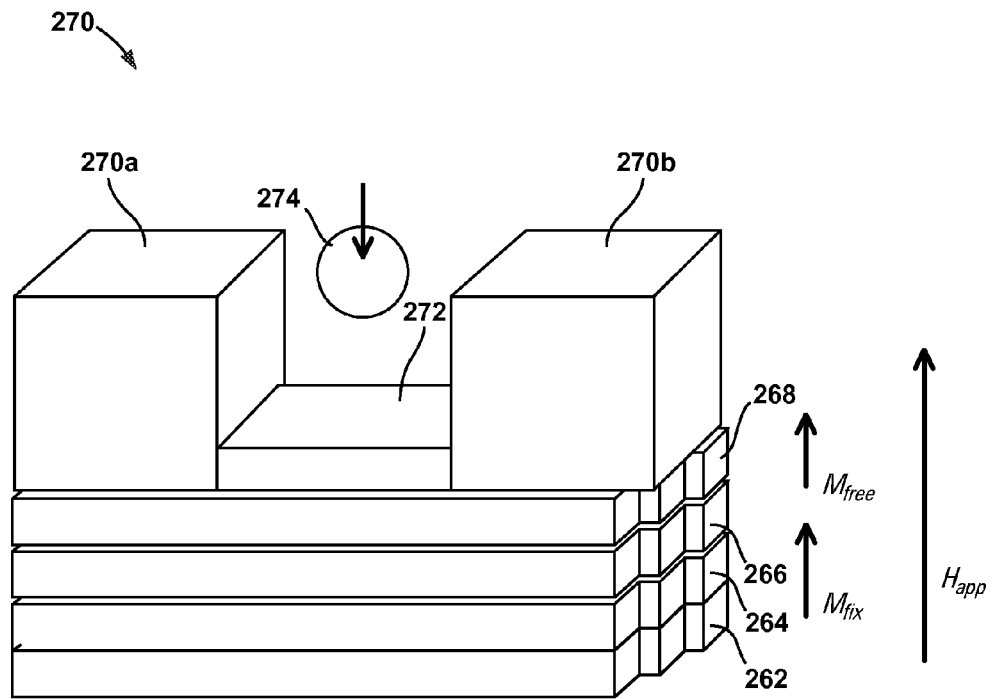
FIG. 19 is a conceptual diagram of an example magnetic biosensor with perpendicular magnetic anisotropy, including with an out-of-plane magnetic moment in the fixed layer and an out-of-plane magnetic moment in the free layer.

FIG. 19 is a conceptual diagram of an example magnetic biosensor 260 with perpendicular magnetic anisotropy, including an out-of-plane magnetic moment in fixed layer 264 and an out-of-plane magnetic moment in a free layer 268. Magnetic biosensor 260 may be substantially similar to magnetic biosensor 80 of FIG. 6, apart from the differences in magnetic anisotropy of fixed layer 264 and free layer 268.

Figure 20:
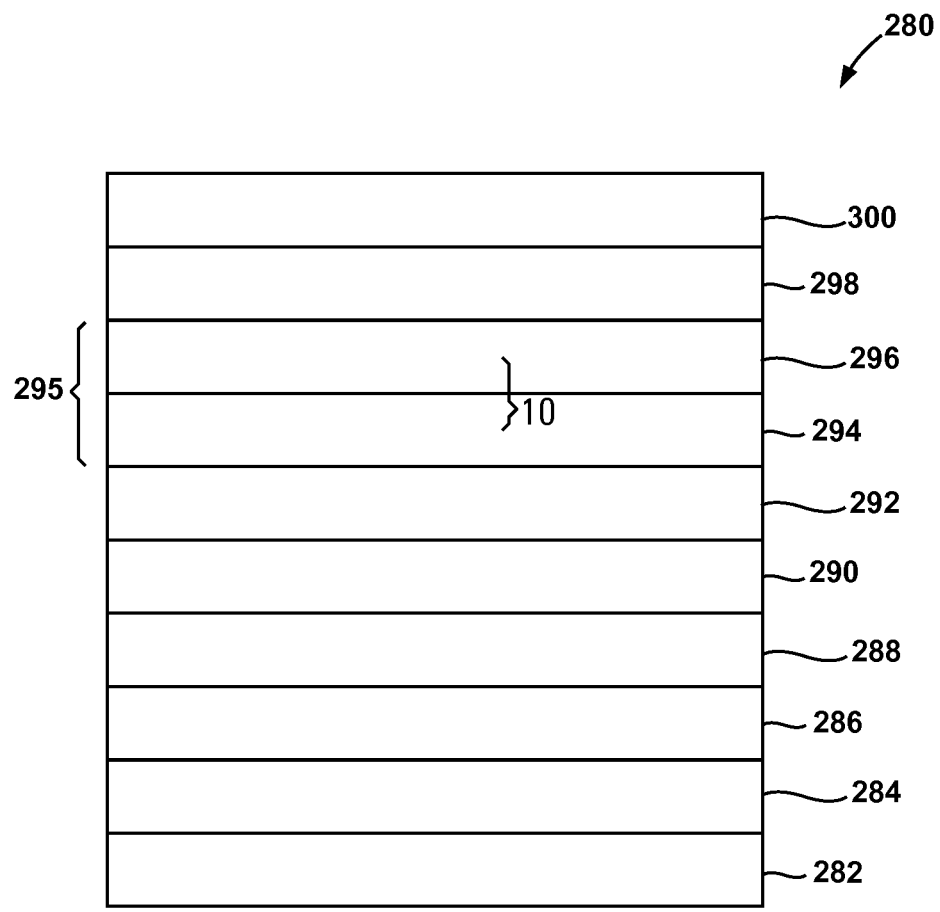
FIG. 20 is a conceptual diagram of an example magnetic tunnel junction stack for a magnetic biosensor with perpendicular magnetic anisotropy, including an out-of-plane magnetic moment in the fixed layer and an out-of-plane magnetic moment in the free layer.

FIG. 20 is conceptual diagram of an example magnetic tunnel junction stack for a magnetic biosensor with perpendicular magnetic anisotropy, including an out-of-plane magnetic moment in the fixed layer and an out-of-plane magnetic moment in the free layer, similar to magnetic biosensor 260 of FIG. 19. Magnetic tunnel junction stack 280 includes a top lead 300 and bottom lead 282, which are used to make electrical connection to magnetic tunnel junction stack 280. Hence, bottom lead 282 and top lead 300 may include an electrically conductive metal. Each of bottom lead 282 and top lead 300 are next to a layer of tantalum (Ta) 284 and 298, respectively, which each have a thickness of about 5 nm. Formed on bottom layer of Ta 284 is a free layer 286 comprising a CoFeB alloy, such as $Co_{20}Fe_{60}B_{20}$.

A nonmagnetic layer 288 is formed on free layer 286 and may include a nonmagnetic material, such as MgO. In some examples, a nonmagnetic layer 288 of MgO may have a resistivity of about 7 $\Omega$-um$^2$. Fixed layer 290 is formed on nonmagnetic layer 288. Fixed layer 290 may include a magnetic material, such as a CoFeB alloy. One example of a CoFeB alloy is $Co_{20}Fe_{60}B_{20}$. Fixed layer 290 may have a selected thickness, such as about 1.5 nm. Fixed layer 290 is antiferromagnetically coupled to a Co/Pd multilayer structure 295 by a layer of ruthenium (Ru) 292. In some examples, the layer of Ru 292 is about 0.3 nm thick. Co/Pd multilayer structure 295 may include a plurality of pairs of Co layers 294 and Pd layers 296, such as, for example, 10 layer pairs. In some examples, the thickness of each Co layer 294 is about 0.3 nm and the thickness of each Pd layer 296 is about 1.0 nm. Top layer of Ta 298 is formed on the top Pd layer 298. This magnetic tunnel junction stack 280 is configured with materials for creating perpendicular anisotropy in fixed layer 290 and free layer 286. In some examples, magnetic stack 280 may be annealed at a temperature of about 200° C. at a pressure of about $1 \times 10^{-6}$ Torr for about 2 hours during formation of the stack 280. Magnetic tunnel junction stack 280 may be used in any of the magnetic biosensors described herein.

Figure 21:
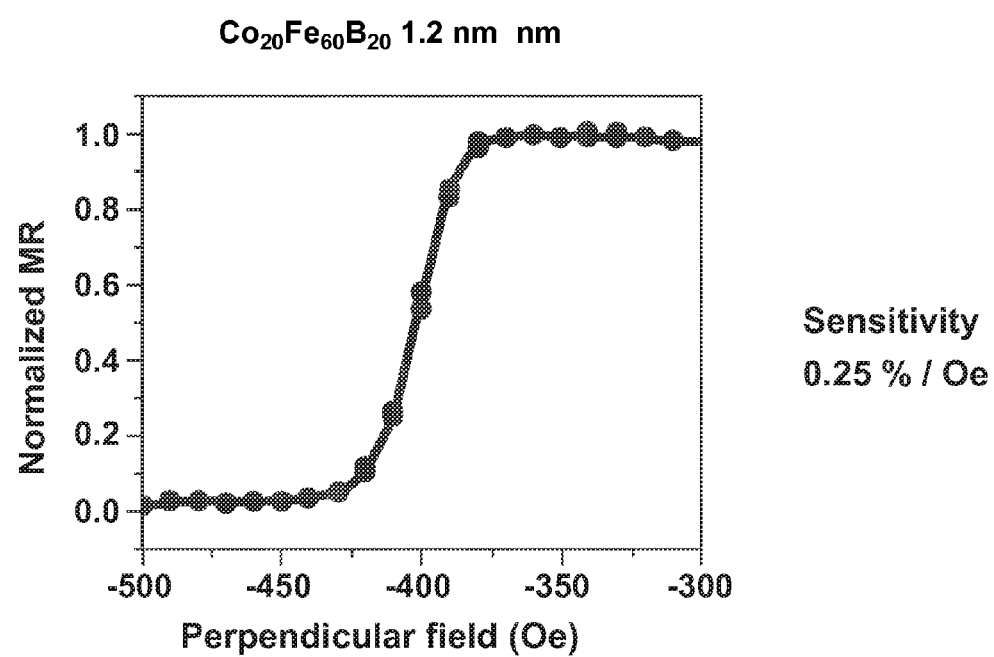
FIG. 21 is a diagram of an example normalized tunneling magnetoresistance (TMR) versus applied magnetic field curve in response to an out-of-plane applied magnetic field for a magnetic biosensor consistent with the example shown in FIG. 20.

FIG. 21 is a diagram of an example normalized tunneling magnetoresistance (TMR) versus applied magnetic field curve in response to an out-of-plane applied magnetic field for a magnetic biosensor consistent with the example shown in FIG. 20. In some example magnetic tunnel junction stack 280 tested to produce the curve in FIG. 21, free layer 286 had a thickness of about 1.2 nm. The y-axis contains the values for normalized magnetic-resistance (MR). The x-axis shows the perpendicular field (Oe). The sensitivity of magnetic tunnel junction stack 280 in the example shown in FIG. 21 is approximately 0.25%/Oe.

Figure 22:
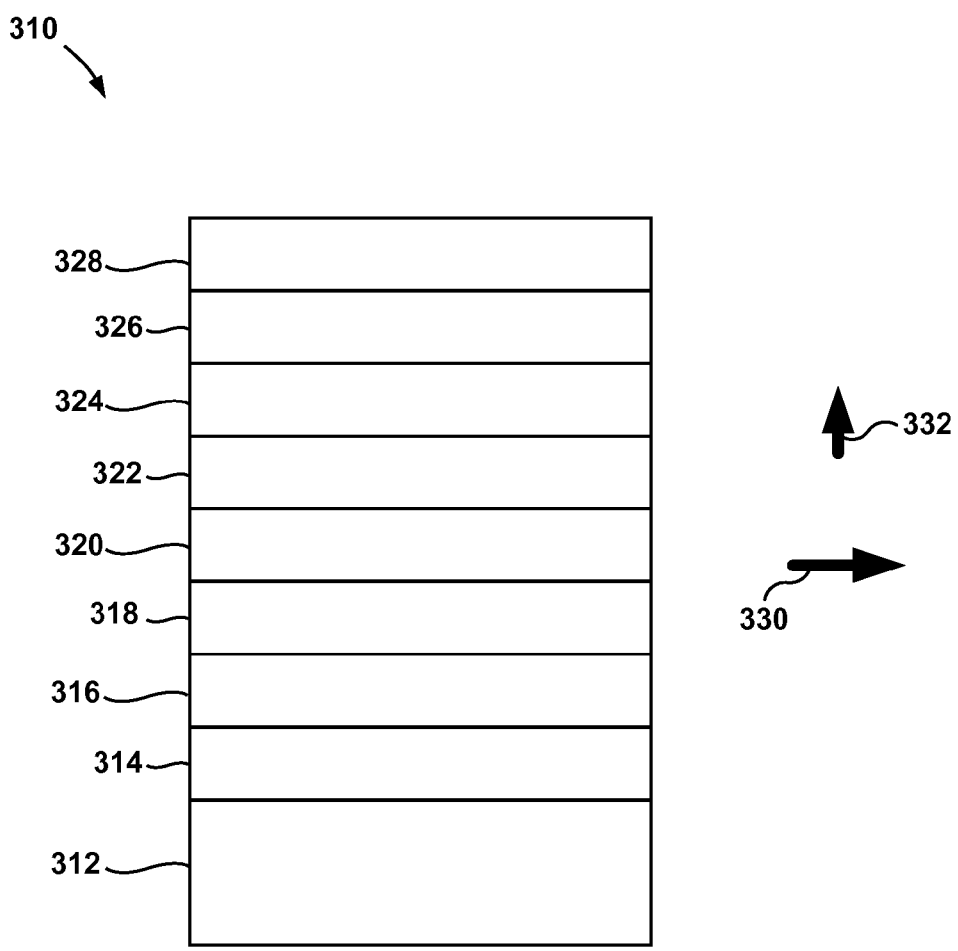
FIG. 22 is a conceptual diagram of another example magnetic tunnel junction stack that may be used in a magnetic biosensor that has an external magnetic field applied in a direction substantially perpendicular to the magnetic stack.

FIG. 22 is a conceptual diagram of another example magnetic tunnel junction stack that may be used in a magnetic biosensor that has an external magnetic field applied in a direction substantially perpendicular to the magnetic stack. Magnetic tunnel junction stack 310 includes a bottom lead 312 that is formed of alternating layers of tantalum (Ta) and ruthenium (Ru) in an order of Ta/Ru/Ta/Ru/Ta, each layer about 5 nm thick. Magnetic tunnel junction stack 310 also includes a top lead 328, which may be formed similar to bottom lead 312 or using a different material composition. Bottom lead 312 and top lead 328 are used to make electrical connection to magnetic tunnel junction stack 310.

Formed on bottom lead 312 is a 17 nm thick platinum-manganese (PtMn) layer 314. A 2.5 nm thick cobalt-iron (CoFe) layer 316 is formed on PtMn layer 314. A fixed layer 320 comprising a cobalt-iron-boron (CoFeB) alloy is anti-ferromagnetically coupled to CoFe layer 316 and PtMn layer 314 by a 0.85 nm thick ruthenium (Ru) layer 318. Fixed layer 320 may have a thickness of about 3 nm and magnetic anisotropy in the plane of fixed layer 320. Hence, a magnetic moment 330 of fixed layer 320 may be substantially fixed in an in-plane orientation.

A MgO nonmagnetic layer 322 is formed on fixed layer 320, and is about 1.7 nm thick. Formed on MgO nonmagnetic layer 322 is a free layer 324 comprising a CoFeB alloy. Free layer 324 has a thickness of about 1.1 nm. Free layer 324 has a magnetic moment 332 that has magnetically stable states in antiparallel directions substantially perpendicular to the major plane of free layer 324. Magnetic stack 326 also includes a top layer of tantalum (Ta) formed between free layer 324 and top lead 328. Magnetic stack 310 may be used in any of the magnetic biosensors described herein.

Figure 23:
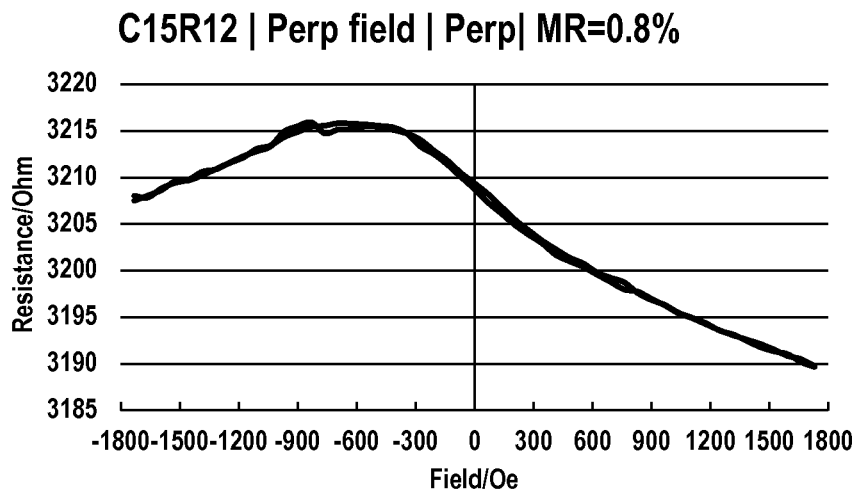
FIG. 23 is a diagram of an example magnetoresistance versus applied magnetic field curve in response to an out-of-plane applied magnetic field for a magnetic tunnel junction stack consistent with the example shown in FIG. 22.
Figure 24:
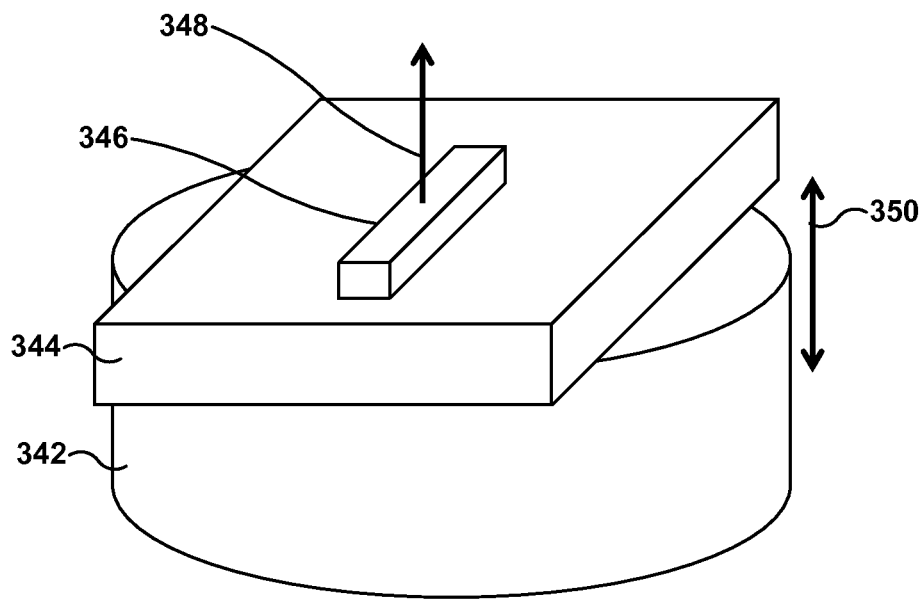
FIG. 24 is a conceptual diagram illustrating an example configuration of a magnetic tunnel junction stack and a magnetic field source used for generating the magnetoresistance versus applied magnetic field curve shown in FIG. 23.

FIG. 23 is a diagram of an example magnetoresistance versus applied magnetic field curve in response to an out-of-plane applied magnetic field for a magnetic tunnel junction stack consistent with the example shown in FIG. 22. FIG. 24 is a conceptual diagram illustrating an example configuration of a magnetic tunnel junction stack and a magnetic field source used for generating the magnetoresistance versus applied magnetic field curve shown in FIG. 23. As shown in FIG. 24, an electromagnet 342 is configured to generate a magnetic field 350 that is substantially perpendicular to a major plane of stage 344 and magnetic stack 346. Magnetic stack 346 has an easy axis 348 defined by shape anisotropy of magnetic stack 346. The results of applying a changing magnetic field 350 to magnetic stack 346 are shown in FIG. 23, and illustrate a relatively large substantially linear portion of the curve with a normalized magnetic-resistance of about 0.8%.

Figure 25:
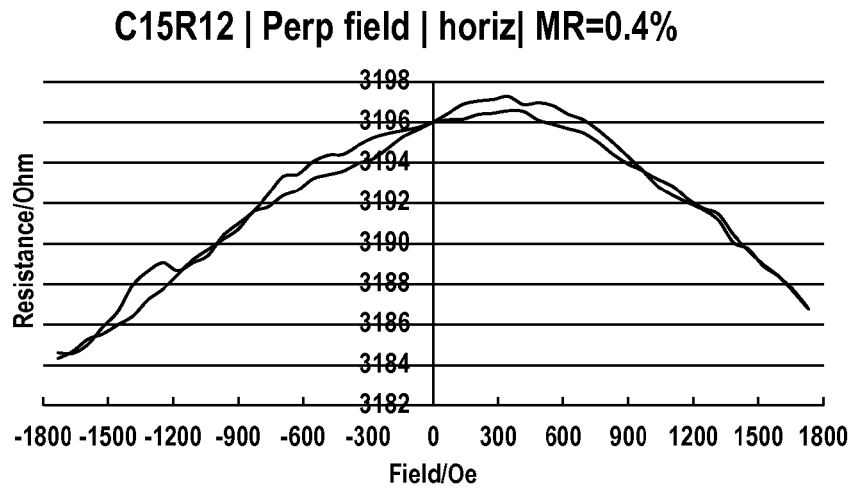
FIG. 25 is a diagram of an example magnetoresistance versus applied magnetic field curve in response to an out-of-plane applied magnetic field for a magnetic tunnel junction stack consistent with the example shown in FIG. 22.
Figure 26:
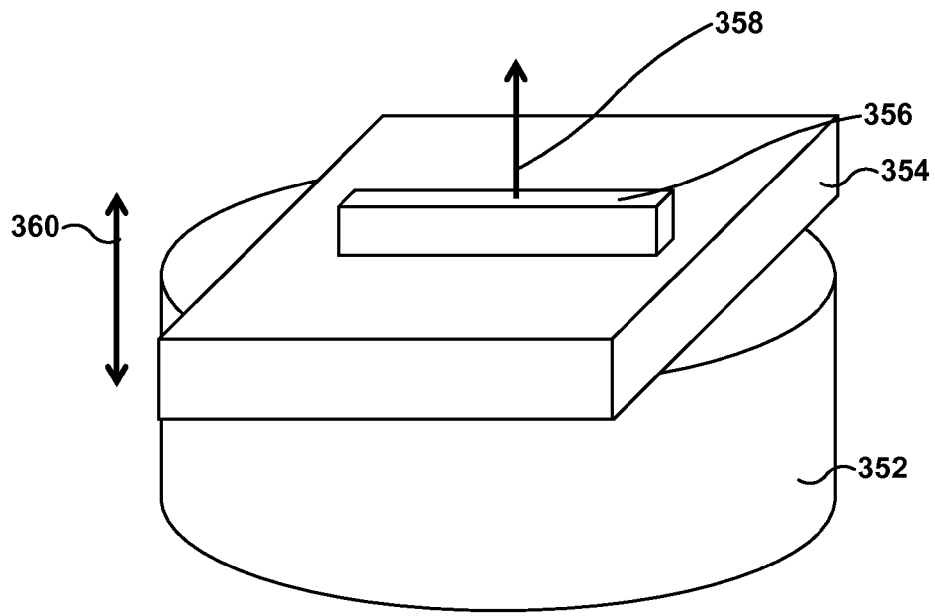
FIG. 26 is a conceptual diagram illustrating an example configuration of a magnetic tunnel junction stack and a magnetic field source used for generating the magnetoresistance versus applied magnetic field curve shown in FIG. 25.

FIG. 25 is a diagram of an example magnetoresistance versus applied magnetic field curve in response to an out-of-plane applied magnetic field for a magnetic tunnel junction stack consistent with the example shown in FIG. 22. FIG. 26 is a conceptual diagram illustrating an example configuration of a magnetic tunnel junction stack and a magnetic field source used for generating the magnetoresistance versus applied magnetic field curve shown in FIG. 25. As shown in FIG. 26, an electromagnet 352 is configured to generate a magnetic field 360 that is substantially perpendicular to a major plane of stage 354 and magnetic stack 356. Magnetic stack 356 has an easy axis 358 defined by shape anisotropy of magnetic stack 356. The results of applying a changing magnetic field 360 to magnetic stack 356 are shown in FIG. 25, and illustrate a relatively large substantially linear portion of the curve with a normalized magnetic-resistance of about 0.4%.

Figure 27:
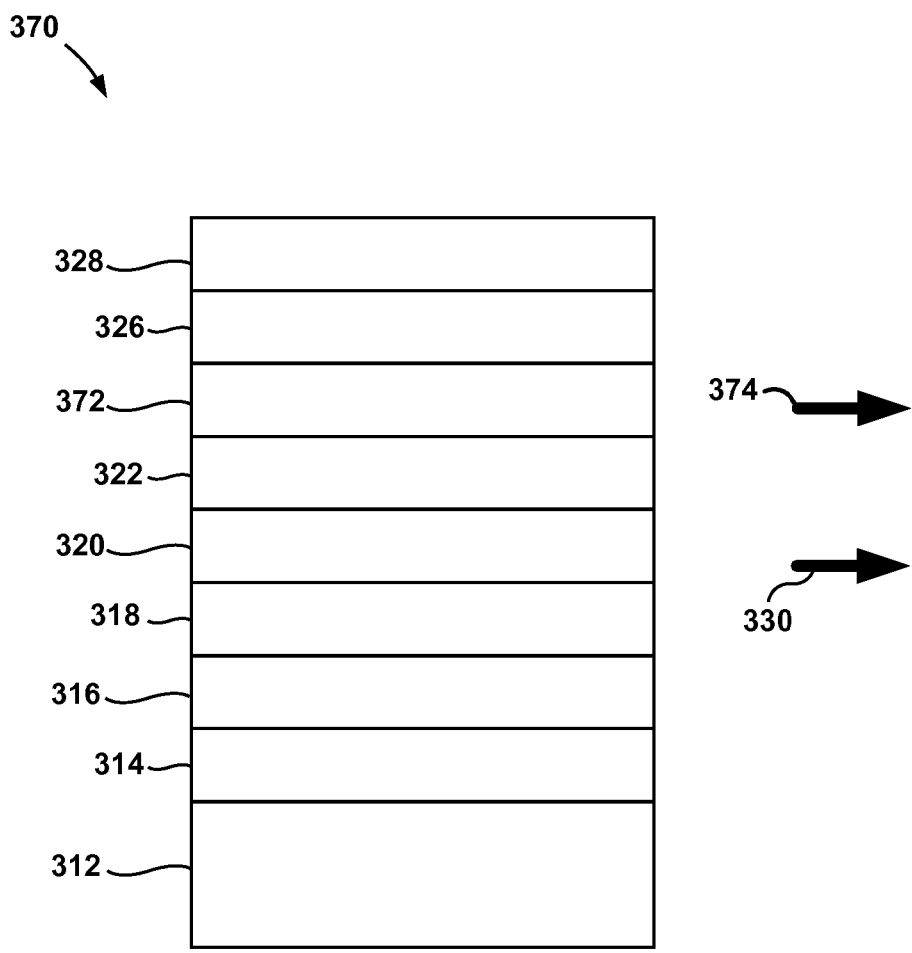
FIG. 27 is a conceptual diagram of another example magnetic tunnel junction stack that may be used in a magnetic biosensor that has an external magnetic field applied in a direction substantially perpendicular to the magnetic stack.

FIG. 27 is a conceptual diagram of another example magnetic tunnel junction stack 370 that may be used in any of the magnetic biosensors described herein that has an external magnetic field applied in a direction substantially perpendicular to the magnetic stack. Magnetic tunnel junction stack 370 is generally similar to magnetic tunnel junction stack 310 described with respect to FIG. 22, aside from the differences noted herein.

Free layer 372 is formed on MgO nonmagnetic layer 322. Free layer 372 comprises a CoFeB alloy and has a thickness of about 1.7 nm. Free layer 324 has a magnetic moment 374 that has magnetically stable states in antiparallel directions substantially parallel to the major plane of free layer 372. Magnetic stack 370 may be used in any of the magnetic biosensors described herein.

Figure 28:
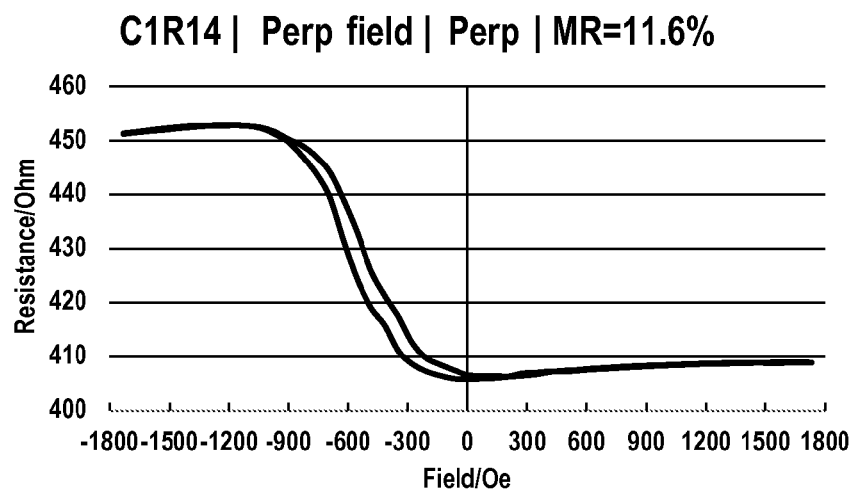
FIG. 28 is a diagram of an example magnetoresistance versus applied magnetic field curve in response to an out-of-plane applied magnetic field for a magnetic tunnel junction stack consistent with the example shown in FIG. 27.
Figure 29:
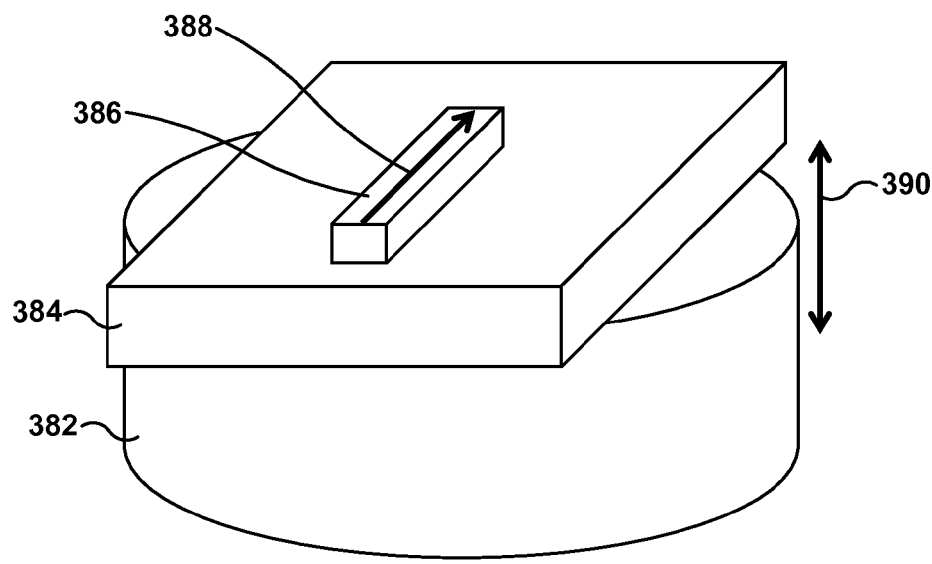
FIG. 29 is a conceptual diagram illustrating an example configuration of a magnetic tunnel junction stack and a magnetic field source used for generating the magnetoresistance versus applied magnetic field curve shown in FIG. 28.

FIG. 28 is a diagram of an example magnetoresistance versus applied magnetic field curve in response to an out-of-plane applied magnetic field for a magnetic tunnel junction stack consistent with the example shown in FIG. 27. FIG. 29 is a conceptual diagram illustrating an example configuration of a magnetic tunnel junction stack and a magnetic field source used for generating the magnetoresistance versus applied magnetic field curve shown in FIG. 28. As shown in FIG. 29, an electromagnet 382 is configured to generate a magnetic field 390 that is substantially perpendicular to a major plane of stage 384 and magnetic stack 386. Magnetic stack 386 has an easy axis 388 defined by shape anisotropy of magnetic stack 386. The results of applying a changing magnetic field 390 to magnetic stack 386 are shown in FIG. 28, and illustrate a relatively large substantially linear portion of the curve with a normalized magnetic-resistance of about 11.6%.

Figure 30:
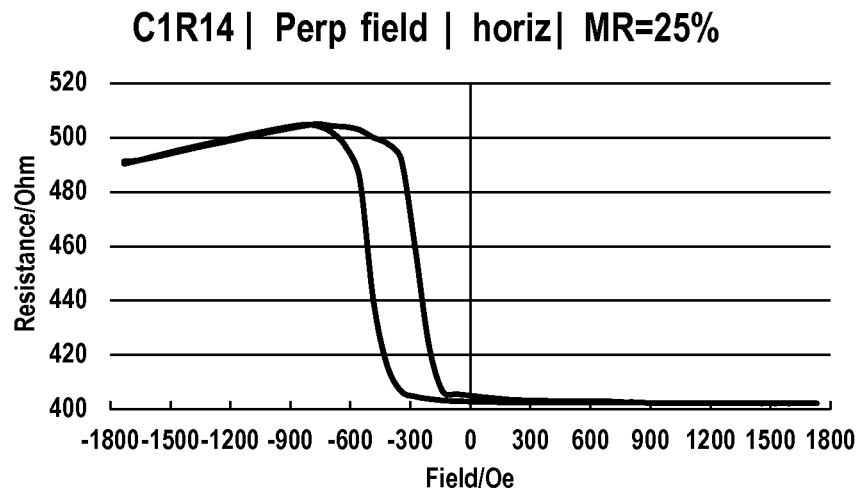
FIG. 30 is a diagram of an example magnetoresistance versus applied magnetic field curve in response to an out-of-plane applied magnetic field for a magnetic tunnel junction stack consistent with the example shown in FIG. 27.
Figure 31:
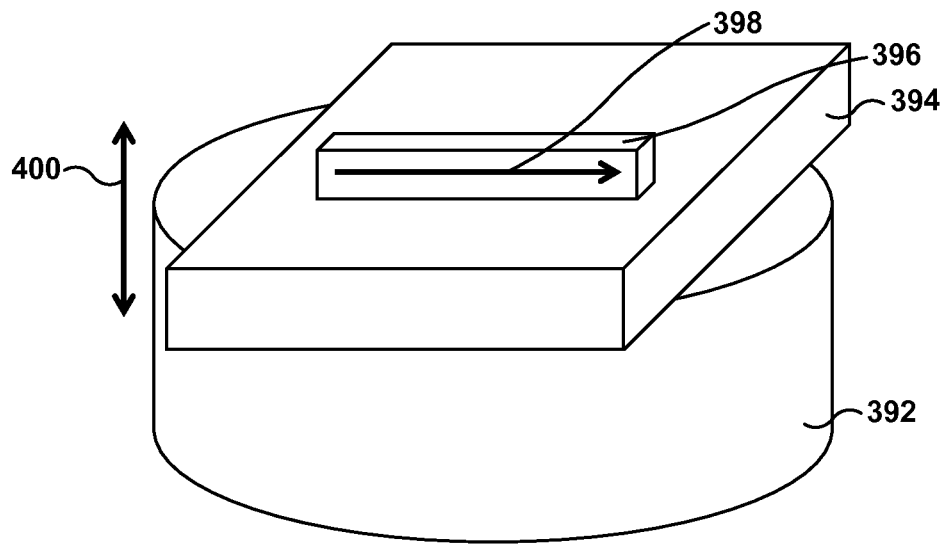
FIG. 31 is a conceptual diagram illustrating an example configuration of a magnetic tunnel junction stack and a magnetic field source used for generating the magnetoresistance versus applied magnetic field curve shown in FIG. 30.

FIG. 30 is a diagram of an example magnetoresistance versus applied magnetic field curve in response to an out-of-plane applied magnetic field for a magnetic tunnel junction stack consistent with the example shown in FIG. 27. FIG. 31 is a conceptual diagram illustrating an example configuration of a magnetic tunnel junction stack and a magnetic field source used for generating the magnetoresistance versus applied magnetic field curve shown in FIG. 30. As shown in FIG. 31, an electromagnet 392 is configured to generate a magnetic field 400 that is substantially perpendicular to a major plane of stage 394 and magnetic stack 396. Magnetic stack 396 has an easy axis 398 defined by shape anisotropy of magnetic stack 396. The results of applying a changing magnetic field 400 to magnetic stack 396 are shown in FIG. 30, and illustrate a substantially linear portion of the curve with a normalized magnetic-resistance of about 25%.

Figure 32:
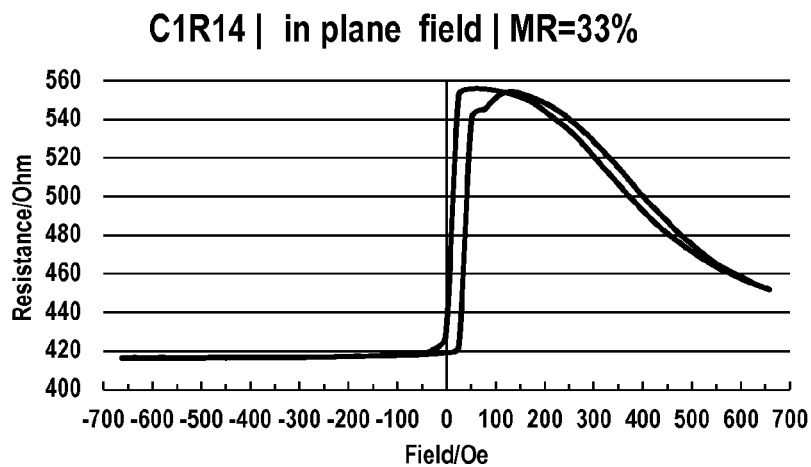
FIG. 32 is a diagram of an example magnetoresistance versus applied magnetic field curve in response to an in-plane applied magnetic field for a magnetic tunnel junction stack consistent with the example shown in FIG. 27.
Figure 33:
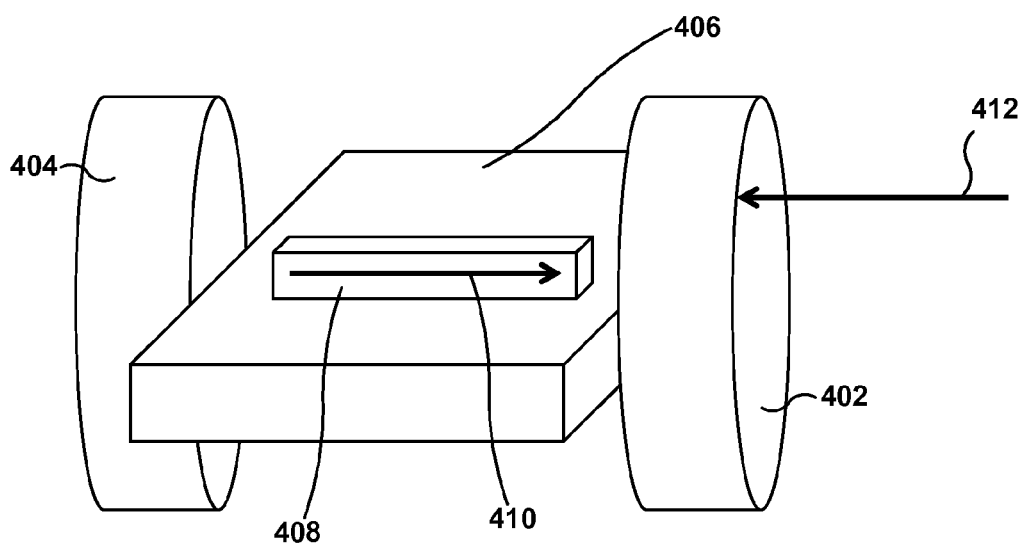
FIG. 33 is a conceptual diagram illustrating an example configuration of a magnetic tunnel junction stack and a magnetic field source used for generating the magnetoresistance versus applied magnetic field curve shown in FIG. 32.

FIG. 32 is a diagram of an example magnetoresistance versus applied magnetic field curve in response to an in-plane applied magnetic field for a magnetic tunnel junction stack consistent with the example shown in FIG. 27. FIG. 33 is a conceptual diagram illustrating an example configuration of a magnetic tunnel junction stack and a magnetic field source used for generating the magnetoresistance versus applied magnetic field curve shown in FIG. 32. As shown in FIG. 33, a first electromagnet 402 and a second electromagnet 404 are configured to generate a magnetic field 412 that is substantially parallel to a major plane of stage 406 and magnetic stack 408. Magnetic stack 408 has an easy axis 140 defined by shape anisotropy of magnetic stack 408. The results of applying a changing magnetic field 412 to magnetic stack 408 are shown in FIG. 32, and illustrate a substantially linear portion of the curve with a normalized magnetic-resistance of about 33%.

Figure 34:
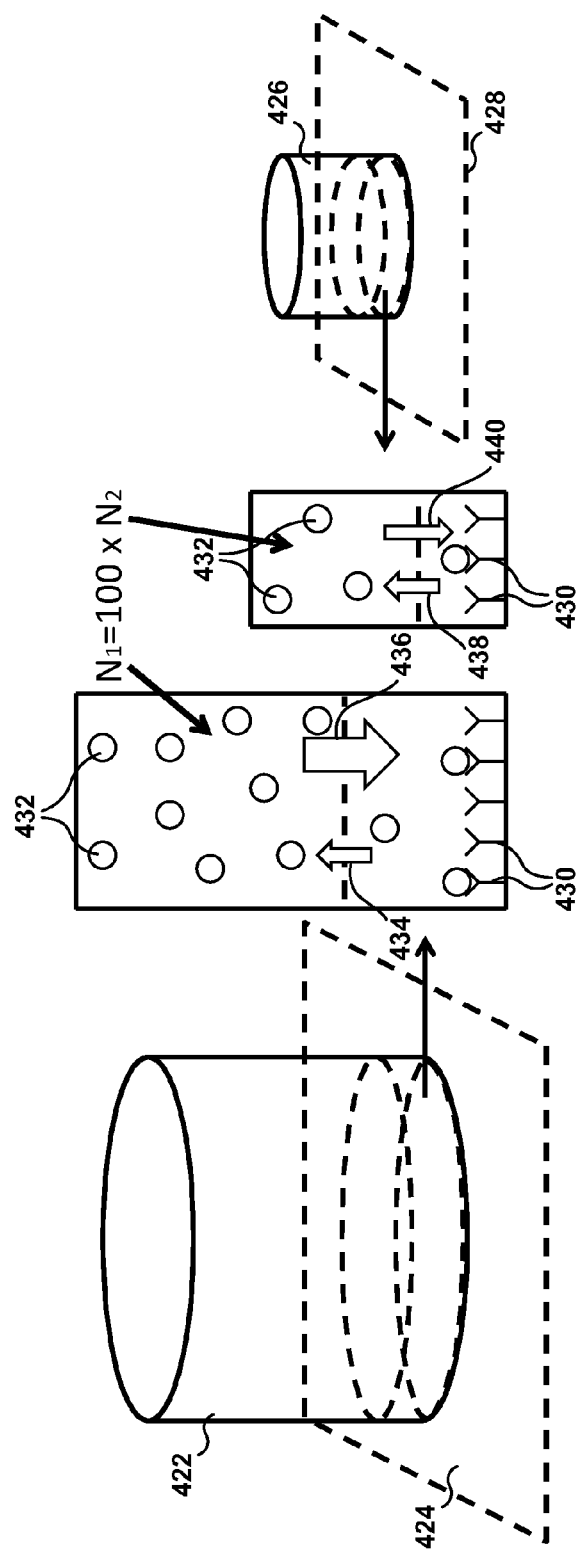
FIG. 34 is a conceptual diagram that illustrates differences between reaction containers of different sizes.

As described above, magnetic biosensors may include a reaction container, such as a reaction well. Different sizes of reaction containers may be adapted for different uses. For examples, while small reaction containers, e.g., 40 µL reaction containers, may be well adapted for drug discovery or the like. However, reaction containers of this size may not be as well adapted for other uses, such as blood testing. In some examples, larger reaction containers may be better suited for testing like blood testing. FIG. 34 is a conceptual diagram that illustrates differences between reaction containers of different sizes.

In the example of FIG. 34, the reaction containers are reaction wells. Reaction well 422 is a larger reaction container and may be capable of holding, for example, about 4 mL of fluid. Reaction well 422 is attached to a magnetic biosensor or magnetic biosensor array 424. As described above, in some implementations, magnetic biosensor array 424 may include a plurality of biosensors, and each biosensor may be configured to detect a similar analyte or a different analyte.

Reaction well 426 is a smaller reaction container and may be capable of holding, for example, about 40 µL of fluid. Reaction well 426 is attached to a magnetic biosensor or magnetic biosensor array 428. Similar to magnetic biosensor array 424, in some implementations, magnetic biosensor array 428 may include a plurality of biosensors, and each biosensor may be configured to detect a similar analyte or a different analyte.

Each of reaction wells 422 and 426 include a plurality of capture antibodies 430 bound to a surface of sensor 424 within the volume enclosed by the respective reaction well 422 or 426. Additionally, each of reaction wells 422 and 426 contains a sample including a plurality of antigens 432. Because the volume of the sample is about 100 times greater in reaction well 422 than in reaction well 426, reaction well 422 contains about 100 times as many antigens 432 as reaction well 426 when the concentration of antigens 432 is the same in each sample.

Arrows 434 and 436 illustrate the relative strength of Brownian motion in the sample within reaction well 422. Because antigens 432 near capture antibodies 430 have a chance of binding to capture antibodies 430, a lower concentration region (of antigens 432) will form just above capture antibodies 430 (compared to the bulk concentration of antigens 432 in the sample). This will lead to an imbalance of Brownian motion (i.e., diffusion) toward capture antibodies 430, as indicated by arrows 434 and 436. This tends to continue to drive motion of antigens 432 toward capture antibodies 430, which may improve a chance of antigens 432 binding to capture antibodies 430.

However, in a reaction well 426, there are a smaller number of antigens 432. Hence, when antigens 432 bind to capture antibodies 430 within reaction well 426, a smaller depletion zone is formed above capture antibodies 430, and concentration equilibrium is reached sooner than in reaction well 422. This may lower a chance of antigens 432 binding to capture antibodies 430. Based on this observation, it may be preferable to use a larger reaction well 422 when testing samples with a low expected concentration of antigen 432.

Figure 35:
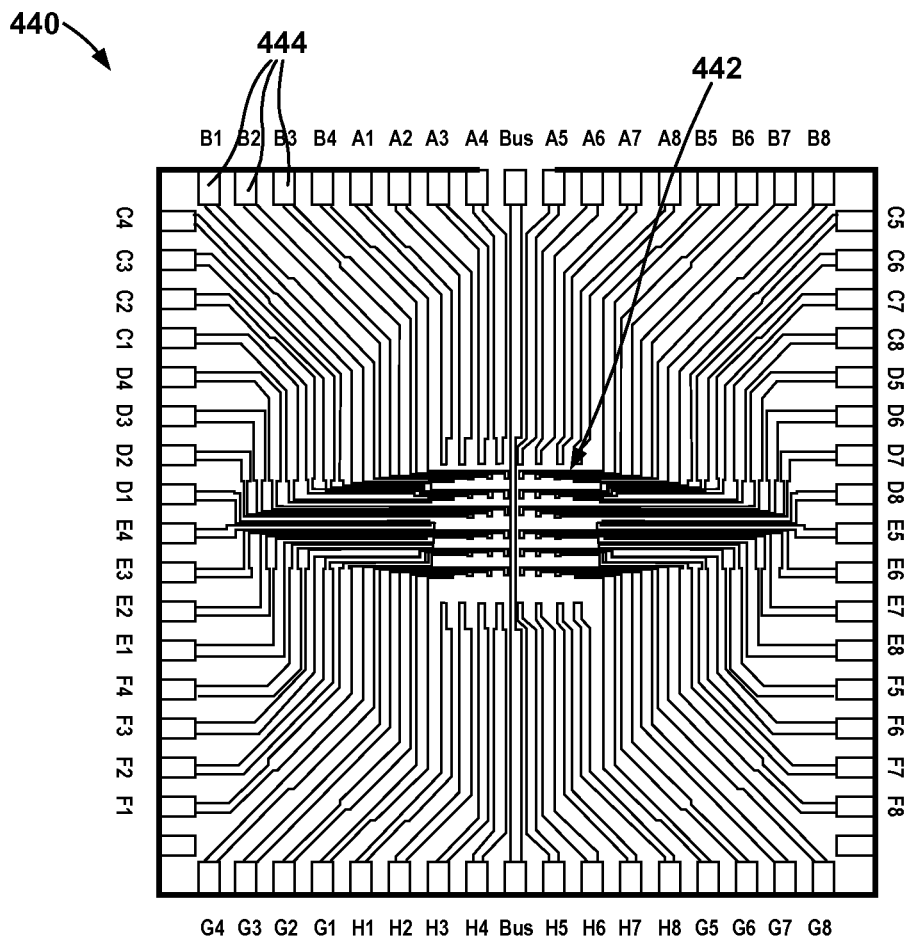
FIG. 35 is a conceptual diagram of an example magnetic biosensor array that includes a plurality of individual magnetic biosensors.

FIG. 35 is a conceptual diagram of an example magnetic biosensor array that includes a plurality of individual magnetic biosensors. One possible layout for a magnetic biosensor array 440 could include 320 sensors disposed in sensor region 442 and a similar number of electrodes 444 (and, optionally, additional bus lines) in one die (chip or substrate). In some examples, the additional electrodes (e.g., electrodes 444 in excess of the number sensors) can be used for energizing, controlling, or grounding magnetic biosensor 440. In some implementations, magnetic biosensor array 440 measures about 80 mm by about 80 mm. Such a magnetic biosensor array 440 may be used with a sample well (not shown in FIG. 35) that has a volume of about 4 mL (e.g., a well with a radius of about 25 mm and a height of about 2 mm.

Figure 36:
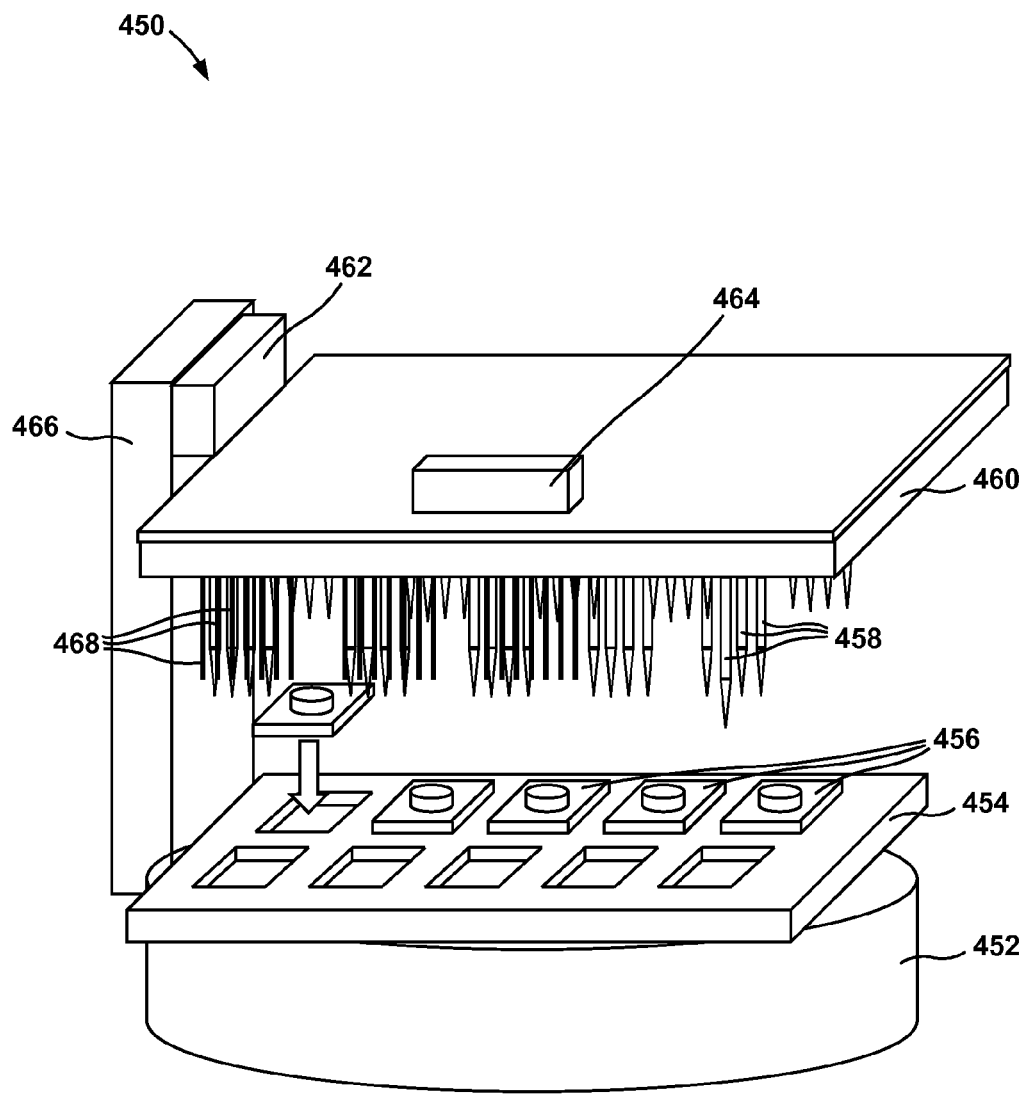
FIG. 36 is a conceptual diagram of an example magnetic biosensing system that includes a plurality of dispensers for dispensing samples into a plurality of sample containers.

In some examples, in addition to automated testing of a plurality of samples in parallel, a system may include an automated sample dispensing mechanism. FIG. 36 is a conceptual diagram of an example magnetic biosensing system that includes a plurality of dispensers for dispensing samples into a plurality of sample containers. In some implementations, magnetic biosensing system 450 of FIG. 35 may be similar to magnetic biosensing system 210 shown in FIG. 4, aside from the differences described herein.

Magnetic biosensing system 450 includes a magnetic field generator 452, which may be a permanent magnetic or an electromagnet. Disposed on a top surface of magnetic field generator 452 is a sample plate 454, which holds a plurality of magnetic biosensor arrays 456. Each of magnetic biosensor arrays 456 includes a reaction well (not labeled in FIG. 35) and a plurality of magnetic biosensors (not labeled in FIG. 35).

Magnetic biosensing system 450 also includes a movable stage 460. Attached to stage 460 are a plurality of sample dispensers 458 and a plurality of probes 468. Stage 460 is movably attached to track 466. First motor 462, which may be a stepper motor, is configured to move stage 460 vertically along track 466 to bring stage 460 toward and away from sample plate 454.

Second motor 464 is configured to controllably extend and retract respective ones of the plurality of sample dispensers 458. In an extended position, sample dispensers 458 may be positioned to dispense a sample or a reagent solution into a respective one of the sample wells. In a retracted position, sample dispensers 458 may be out of the way to allow probes 468 to contact electrical contacts on magnetic biosensors 456, e.g., as described with respect to FIGS. 12A-12D. In some examples, a plurality of sample dispensers 458 may be positioned so when sample dispensers 458 are positioned to dispense a sample into a sample well. In other words, multiple sample dispensers 458 may be positioned above a single sample well. In this way, sample dispensers 458 may allow controllable dispensing of one or more of a plurality of samples into each reaction well. In some implementations, four sample dispensers 458 may be positioned above each sample well, allowing controllable dispensing of one or more of four different solutions into each sample well.

In some examples, magnetic biosensing system 450 may be coupled to a controller or computer (e.g., similar to magnetic biosensing system of FIG. 13). The controller or computer can control dispensing of selected samples from sample dispensers 458 and testing of the samples using magnetic biosensors 456. In this way, magnetic biosensing system 450 may facilitate further automation of the testing process, including dispensing of the samples.

Figure 37:
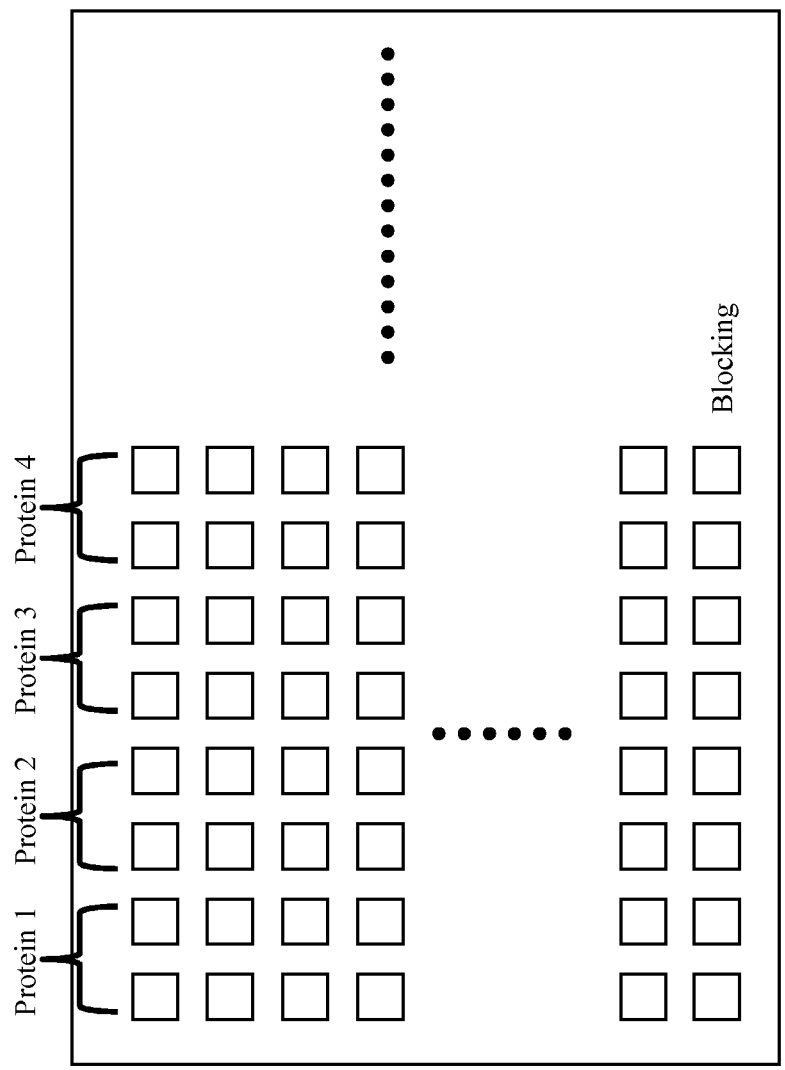
FIG. 37 is a conceptual diagram of an example magnetic biosensor array that can be used for protein multiplexing.

Magnetic biosensors described herein may be utilized in some implementations for protein multiplexing. For example, a magnetic biosensor array associated with a sample container that holds a larger amount of sample, e.g., 4 mL, may be used for protein multiplexing. FIG. 37 is a conceptual diagram of an example magnetic biosensor array that can be used for protein multiplexing. In some examples, a magnetic biosensor array can include 320 individual magnetic biosensors. As shown in FIG. 37, in some implementations, two adjacent columns of magnetic biosensors can be printed with one capture antibody configured to detect a specific protein. Different capture antibodies may be printed in different column pairs. Each of the capture antibodies may be configured to capture a different protein. In some examples, the last row of each column is reserved for blocking control sensors.

Figure 38:
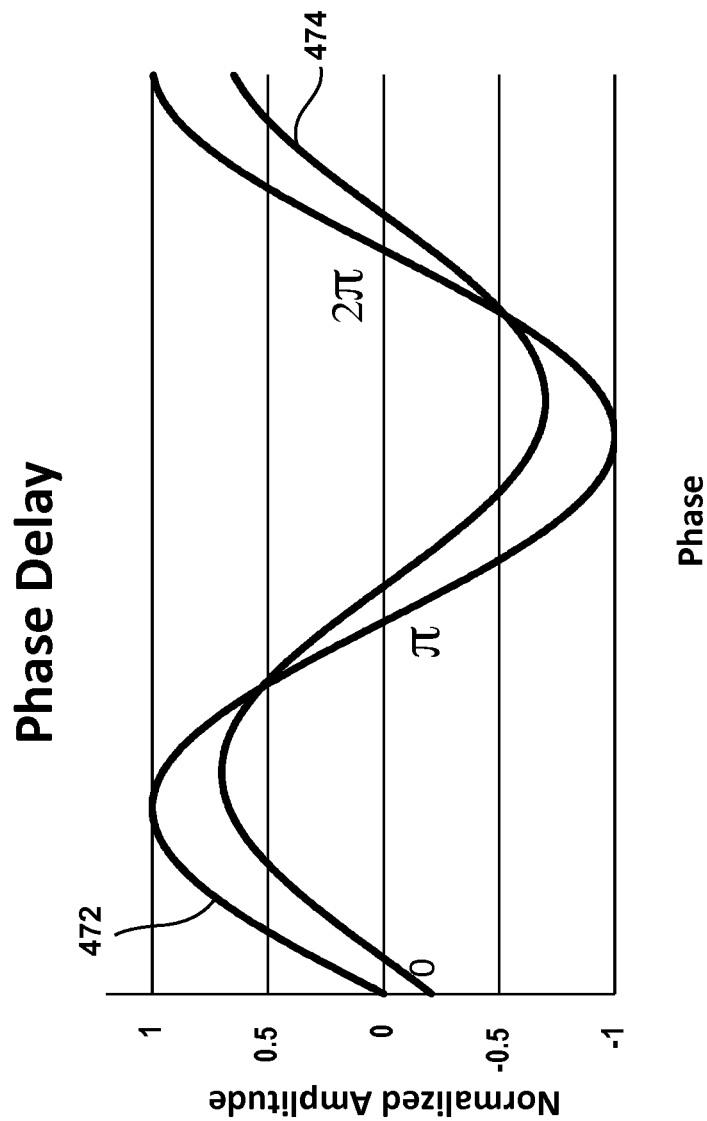
FIG. 38 is an example plot of normalized amplitude versus phase that shows an effect of bonded magnetically marked antigens on an alternating current signal.

In some implementations, coloring may be used to detect specific binding with different antigens in a single sample. FIG. 38 is an example plot of normalized amplitude versus phase that shows an effect of bonded magnetic marked antigens on an alternating current signal. The phase may be measured directly using the following technique. First a DC current is applied to a magnetic stack of a magnetic biosensor. The magnetic biosensor (or, more specifically, the magnetic stack) is exposed to an alternating current (AC) field. The AC signal shown in FIG. 38 comes from the response of sensor. After magnetically marked antigens particles are bound to capture molecules on a surface of the magnetic biosensor, the magnetic nanoparticles (MNPs) cannot rotate as easily as when the MNPs were not bound, but the electron spin of the MNPs still rotates with the changing AC field. By increasing the frequency of AC field, e.g., above about 100 kilohertz (kHz), Neel relaxation of the MNPs will not keep up with the changing AC field. This results in a phase delay (shown in FIG. 38) in the response of the magnetic biosensor. The phase response before 472 and after 474 MNP bonding shows that bonding the MNPs results in a phase delay. The phase response before binding of MNPs to the biosensor may be described mathematically as $H_0 \cos(\omega t)$, where $H_o$ is the applied (external) magnetic field and w is the angular frequency ($2\pi f$, where f is the frequency of the AC field). The phase response after binding of MNPs to the biosensor may be described mathematically as $H_0 \cos(\omega t) - H_{\mathit{eff}} \cos(\omega t + \phi)$, where $H_{\mathit{eff}}$ is the effective magnetic field applied to the biosensor by the MNPs, and $\phi$ is the phase delay. Different MNPs will generate different phase delays. Hence, by labeling specific antibodies (in a three-layer detection scheme) with specific MNPs, the magnetic biosensor can identify particular antigens in the sample.

FIG. 39 is a conceptual diagram that illustrates an example configuration of a magnetic biosensor configured to detect estradiol. Estradiol is a major active hormone binding to the estrogen receptor in breast cancer cells. Even in low concentrations, e.g., between about 1 picomolar (pM) and about 1 nanomolar (nM), estradiol can stimulate tumor growth. Testing for estradiol after drug treatment can be important in preventing further tumor growth.

As shown in FIG. 39, a bottom surface of the sample well is coated with monoclonal anti-rabbit IgG. The sample well is then incubated with tracer, antiserum, and either standard or sample. After incubation, the sample well is washed to remove all unbound reagents. The well is then developed with Ellman's Reagent (5,5'-dithiobis-(2-nitrobenzoic acid) or DTNB), which can quantify the number of concentration of thiol groups bound to the monoclonal anti-rabbit IgG. Alternatively, if the estradiol tracer is replaced with Iodine-125 linked estradiol, this method can be used for radioimmunoassay.

Figure 40:
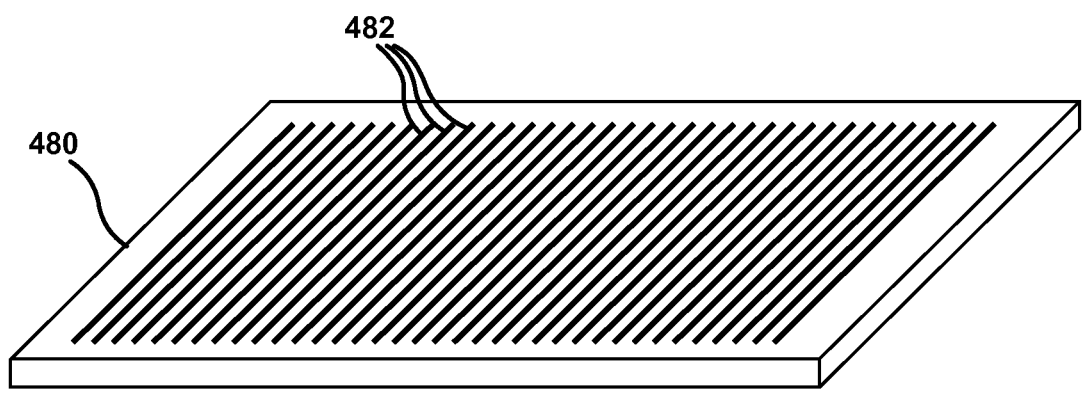
FIG. 40 is a conceptual diagram of an example substrate including a plurality of microfluidic channels.

FIG. 40 is a conceptual diagram of an example substrate 480 including a plurality of microfluidic channels 482. Microfluidic channels 482 may be a type of sample container that can be used with any of the magnetic biosensors described herein. Although not shown in FIG. 40, a plurality of magnetic biosensors may be disposed beneath each of microfluidic channels 482. A bottom surface of each of microfluidic channels 482 may include a plurality of capture antibodies attached to the bottom surface above each of the plurality of magnetic biosensors. In some examples, the plurality of capture antibodies over each of the plurality of magnetic biosensors are the same within one of microfluidic channels 482. In other examples, different capture antibodies may be attached above different magnetic biosensors. Similarly, in some examples, different capture antibodies are attached in different ones of microfluidic channels 482. In other examples, the same capture antibodies are attached in each of microfluidic channels 482.

Microfluidic channels 482 can be used as sample containers for magnetic biosensing systems in a variety of contexts, including basic medical science, disease control and diagnostics, drug discovery, and environment monitoring. Additionally, microfluidic channels 482 may be used to test samples at a range of volumes. In some instances, the dimensions of microfluidic channels 482 may be selected to contain a selected volume. The total volume for which a substrate 480 may be used to test may be increased by, for example, forming more microfluidic channels 482 in substrate 480, increasing a size of microfluidic channels 482, or increasing a flow rate of the sample through microfluidic channels. However, in some examples, one or more of these options to increase a volume of sample tested within a reasonable time period using microfluidic channels 482 may not be viable. In some of these examples, a reaction well or sample well may be used instead, such as reaction well 422 shown in FIG. 34.

Figure 41:
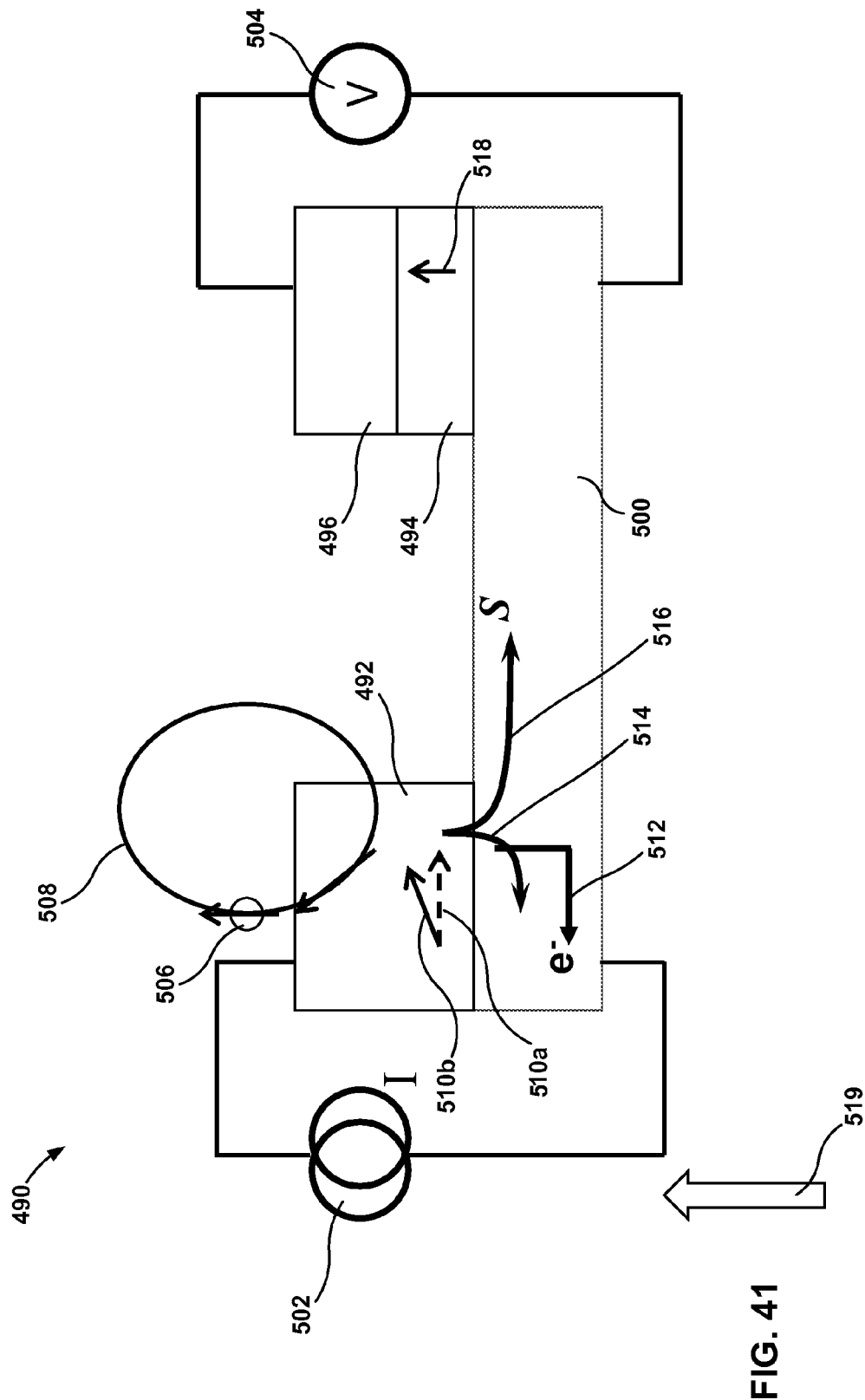
FIG. 41 is a conceptual diagram illustrating another example magnetic biosensor.

FIG. 41 is a conceptual diagram illustrating another example magnetic biosensor. Magnetic biosensor 490 includes a first ferromagnetic layer 492 and a second ferromagnetic layer 494. First ferromagnetic layer 492 may possess a magnetic moment 510 that can rotate under an applied magnetic field (i.e., first ferromagnetic layer 492 is a free layer). In some examples, as shown in FIG. 41, magnetic moment 510 can have a magnetically stable state 510a (in the absence of an applied magnetic field) oriented parallel to the major plane of first ferromagnetic layer 492. In other examples, magnetic moment 510 can have a magnetically stable state 510a (in the absence of an applied magnetic field) oriented out of the major plane of first ferromagnetic layer 492, such as substantially perpendicular to the major plane of first ferromagnetic layer 492

Second ferromagnetic layer 494 may possess a magnetic moment 518 that is substantially fixed in orientation under magnetic fields to which magnetic biosensor 490 is designed to be exposed to during use (i.e., second ferromagnetic layer 494 is a fixed layer). Second ferromagnetic layer 494 is antiferromagnetically coupled to an antiferromagnetic layer 496, which fixes the orientation of magnetic moment 518. As shown in FIG. 41, magnetic moment 518 may, in some examples, be oriented out of the major plane of second ferromagnetic layer 494, such as substantially perpendicular to the major plane of second ferromagnetic layer 494. In other examples, magnetic moment 518 may be oriented parallel to the major plane of second ferromagnetic layer 494.

Each of first ferromagnetic layer 492 and second ferromagnetic layer 494 may be formed from ferromagnetic materials described hereinabove.

A nonmagnetic layer 500 connects first ferromagnetic layer 492 and second ferromagnetic layer 494. First ferromagnetic layer 492 is formed adjacent to a first end of nonmagnetic layer 500 and second ferromagnetic layer 494 is formed adjacent to a second end of nonmagnetic layer 500. In some examples, nonmagnetic layer 500 may be formed of, for example, a semiconductor, such as graphene, molybdenum sulfide ($MoS_2$), or another semiconductor material. In other examples, nonmagnetic layer 500 may be formed of another nonmagnetic material, such as copper (Cu), silver (Ag), or the like.

Although not shown in FIG. 41, a plurality of capture antibodies may be attached to a surface of first ferromagnetic layer or a layer formed above first ferromagnetic layer (e.g., a bottom surface of a sample container (not shown in FIG. 41). The plurality of capture antibodies may be configured to capture or bind to a selected antigen. As describe above, a sample may include the selected antigen, and a reagent may include magnetically marked antigens. One magnetically marked antigen 506 is shown in FIG. 41. Magnetically marked antigen 506 may include a magnetic marker, such as a MNP or a magnetic microsphere bound to the selected antigen.

In use, magnetic biosensor 490 is exposed to an applied perpendicular magnetic field 519 (e.g, a magnetic field oriented substantially perpendicular to a major plane of first magnetic layer 492). A sample and reagent may be placed in the sample container (not shown in FIG. 41) and the selected antigens (magnetically marked or unmarked) may be allowed to bind to the capture antibodies. Depending on the concentration of selected antigens in the sample, a number of magnetically marked antigens 506 may be captured by a corresponding number of capture antibodies. Once the binding is complete, the sample and reagent may be removed from the sample container and the container rinsed to remove any extra unmarked antigens and magnetically marked antigens 506. The above technique is a two-layer technique, similar to that described with reference to FIGS. 2A and 2B. In other examples, magnetic biosensor 490 may be used in a three-layer technique, similar to that described with respect to FIGS. 3A-3D.

As shown in FIG. 41, first ferromagnetic layer 492 may be connected to an electrical current source 502. A current may be applied to first ferromagnetic layer 492 by electrical current source 502 after unmarked antigens and magnetically marked antigens 506 have been allowed to bind to the capture antibodies. Captured magnetically marked antigens 506 generate a magnetic field 508, which may affect an orientation of magnetic moment 510 of first ferromagnetic layer 492. When the electrical current is applied to first ferromagnetic layer 492, charge electrons (represented by line 512) and scattering electrons (represented by line 514) with a certain spin state (e.g., up or down, whichever is more similar to the magnetic orientation of first ferromagnetic layer 492) move in the closed loop circuit that includes first ferromagnetic layer 492. However, scattering electrons with the opposite spin (represented by line 516) will diffuse through graphene layer 500 to the other side of magnetic biosensor 490 (e.g., to the portion of graphene layer adjacent to second ferromagnetic layer 494). The relative orientation of magnetic moment 518 and the spin of the scattering electrons adjacent to second ferromagnetic layer 494 affects the resistance of the closed loop circuit connected to voltage source 504. By measuring this resistance, a concentration of antigen in the sample may be determined, e.g., using a calibration curve as described with respect to FIGS. 2A, 2B, and 3A-3D. The biosensor configuration shown in FIG. 41 may utilize both current perpendicular to the plane (CPP) GMR and MTJ sensor types and may be used with any of the sample containers and/or magnetic biosensing systems described herein.

Figure 42:
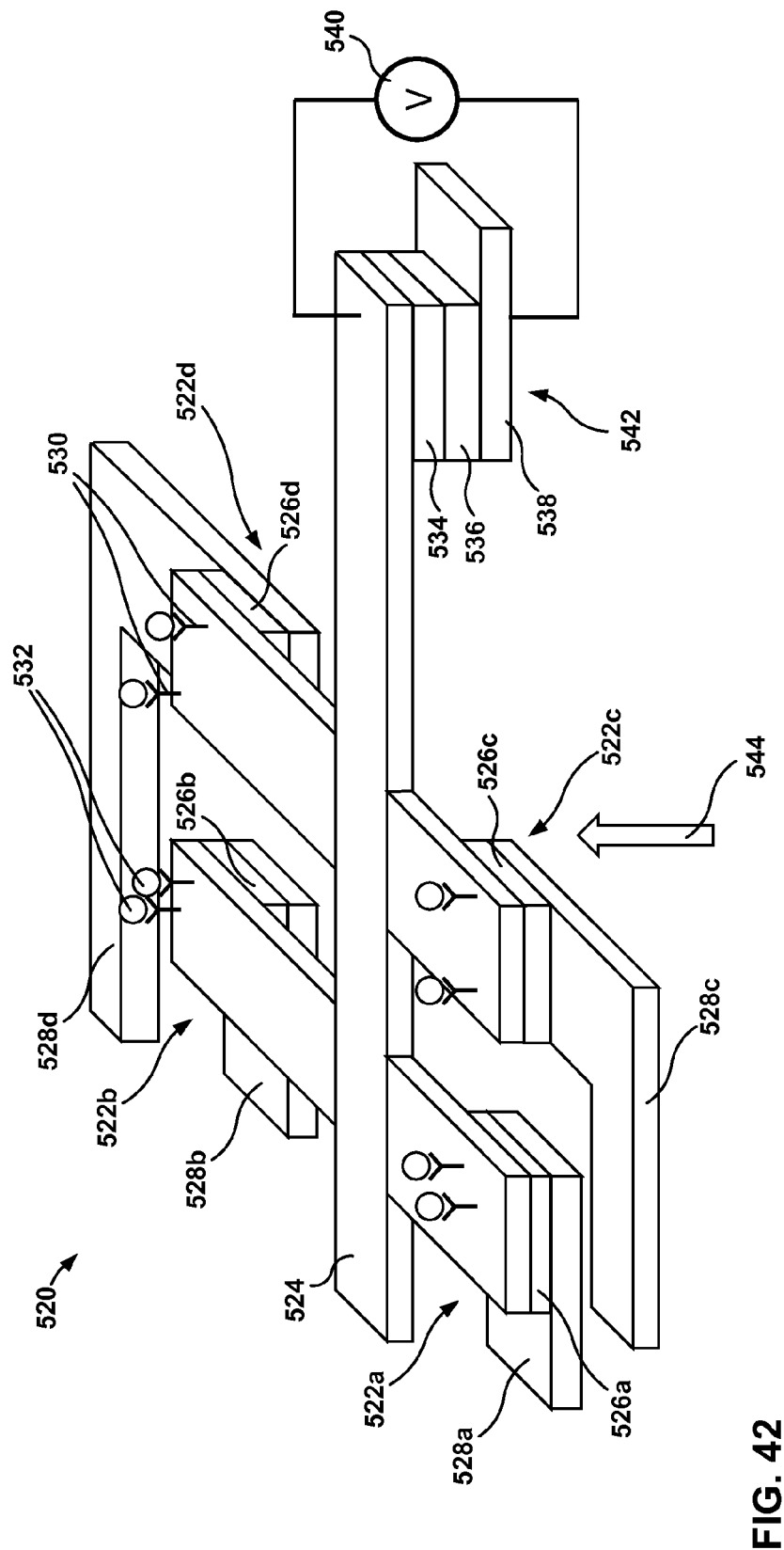
FIG. 42 is a conceptual diagram of a plurality of the sensors depicted in FIG. 41 connected in parallel.

In some examples, biomagnetic sensor 490 may be integrated into a larger sensor that includes a number of sensors 490 connected in parallel. FIG. 42 is a conceptual diagram of a plurality of sensors 490 connected in parallel in a single magnetic biosensor 520. In the example of FIG. 42, a single detection stack 542 is utilized, to which a plurality of sensor stacks 522a-522d (collectively, "sensor stacks 522") are connected. Each of sensor stacks 522 includes a respective one of free magnetic layers 526a-526d (collectively, "free magnetic layers 526"). Each of free magnetic layers 526 is connected to a respective one of bottom electrodes 528a-528d (collectively, "bottom electrodes 528"). Each of bottom electrodes 528 is connected to a current source (not shown in FIG. 42). Each of free magnetic layers 526 is also formed adjacent to (e.g., connected to or near) ends of nonmagnetic layer 524.

Nonmagnetic layer 524 is also connected to detector stack 542. In the example of FIG. 42, another end of nonmagnetic layer 524 is adjacent to (e.g., connected to or near) to fixed magnetic layer 534, which is adjacent to and antiferromagnetically coupled to antiferromagnetic layer 536. Antiferromagnetic layer 536 is attached to a detector electrode 538, which is electrically connected to a voltage source 540. Nonmagnetic layer 524 is also electrically connected to voltage source 540 at a location near detector stack 542.

Additionally, above each of sensor stacks 522 are a plurality of capture antibodies 530. Capture antibodies 530 may be attached to a top surface of nonmagnetic layer 524, as shown in FIG. 42, or to a bottom surface of a sample container placed over biosensor 520.

Similar to biosensor 490 shown in FIG. 41, when magnetically marked antigens 532 have been allowed to bind to the capture antibodies, the magnetic fields generated by the magnetic markers may affect an orientation of a magnetic moment of each of free magnetic layers 526. When an electrical current is applied to each of free magnetic layers 526, e.g., using respective ones of bottom electrodes 528, charge electrons and scattering electrons with a certain spin state (e.g., up or down, whichever is more similar to the magnetic orientation of free magnetic layers 526) move in the closed loop circuit that includes free magnetic layers 526 and bottom electrodes 528. However, scattering electrons with the opposite spin will diffuse through nonmagnetic layer 524 to the other side of magnetic biosensor 520 adjacent to detector stack 542. The relative orientation of the magnetic moment of fixed magnetic layer 534 and the spin of the scattering electrons adjacent to fixed magnetic layer 534 affects the resistance of the detector stack 542 connected to voltage source 540. By measuring this resistance, a concentration of antigen in the sample may be determined, e.g., using a calibration curve as described with respect to FIGS. 2A, 2B, and 3A-3D. Because a plurality of sensor stacks 522 are connected in parallel to a single detector stack 542, magnetic biosensor 520 may be particularly useful for samples with a low concentration of antigen, because the scattering effect at each sensor stack 522 is added at detector stack 542. The biosensor configuration shown in FIG. 42 may utilize both current perpendicular to the plane (CPP)

GMR and MTJ sensor types and may be used with any of the sample containers and/or magnetic biosensing systems described herein.

A number of alternative configurations of magnetic biosensors, magnetic biosensor arrays, and magnetic biosensing systems have been described herein. Although not all possible configurations have been described explicitly as being usable together, one of ordinary skill will appreciate that the various sensors, arrays, and systems may be combined in a number of different ways. Furthermore, although the description has primarily been directed to sample wells, as described above, the magnetic biosensors, magnetic biosensor arrays, and magnetic biosensing systems can be used with microfluidic channels instead of or in addition to sample wells.

Various examples have been described. For example, example magnetic biosensors, biosensor arrays and sensing systems have been described. Any of the examples may be used in conjunction with the other examples. These and other examples are within the scope of the following claims.

What is claimed is:

1. A magnetic biosensing system comprising:
   a probe array comprising a plurality of probes;
   a magnetic biosensor array comprising:
      a plurality of electrical contacts located along at least one peripheral edge of the magnetic biosensor array, wherein the plurality of electrical contacts of the magnetic biosensor array are configured to receive respective ones of the plurality of probes;
      a sample container;
      a plurality of magnetic biosensors each located adjacent to a surface of the sample container, each magnetic biosensor of the plurality of magnetic biosensors comprising a magnetic sensor comprising a free layer and a fixed layer, wherein one of the free layer or the fixed layer has a magnetic moment canted out of a major plane of the free layer or the fixed layer at an inclined angle between 1 and 90 degrees, respectively, in an absence of an external magnetic field, and wherein the other of the free layer or the fixed layer has a magnetic moment oriented parallel to the major plane of the free layer or the fixed layer in the absence of the external magnetic field; and
      a plurality of capture antibodies attached to the surface of the sample container;
   a motor configured to move the probe array toward and away from the magnetic biosensor array to engage and disengage the plurality of probes and the plurality of electrical contacts; and
   a magnetic field generator located below the magnetic biosensor array to apply a magnetic field in a direction perpendicular to a major plane of the magnetic biosensor array.

2. The magnetic biosensing system of claim 1, wherein the magnetic moment of the fixed layer of at least one magnetic biosensor of the plurality of magnetic biosensors in the absence of the external magnetic field is canted out of the major plane of the fixed layer and the magnetic moment of the free layer in the absence of the external magnetic field is oriented parallel to the major plane of the free layer.

3. The magnetic biosensing system of claim 1, wherein the magnetic moment of the free layer of at least one magnetic biosensor of the plurality of magnetic biosensors in the absence of the external magnetic field is canted out of the major plane of the free layer and the magnetic moment of the fixed layer in the absence of the external magnetic field is oriented parallel to the major plane of the fixed layer.

4. The magnetic biosensing system of claim 1, further comprising a current source and a voltage source, wherein each magnetic biosensor of the plurality of magnetic biosensors further comprises:
   a nonmagnetic layer comprising a first end and a second end, wherein the free layer is formed adjacent to the first end and the fixed layer is formed adjacent to the second end,
   a current source coupling electrically coupled to the free layer, the current source, and the first end of the nonmagnetic layer; and
   a voltage source coupling electrically coupled to the fixed layer, the voltage source, and the second end of the nonmagnetic layer, wherein the voltage source is configured to measure a magnetoresistance of the fixed layer and the second end of the nonmagnetic layer.

5. The magnetic biosensing system of claim 1, wherein a respective one or more of the plurality of electrical contacts is electrically coupled to a respective one or more of the plurality of magnetic biosensors, and wherein respective ones of the plurality of electrical contacts are configured to contact respective ones of a plurality of probes to communicate sensed test data to a computing device.

6. The magnetic biosensing system of claim 1, wherein the sample container comprises at least one of a sample well or a microfluidic channel.

7. The magnetic biosensing system of claim 1, wherein the plurality of capture antibodies comprises a first plurality of capture antibodies and a second plurality of capture antibodies, wherein the first plurality of capture antibodies are attached to the bottom surface of the sample container above a first magnetic biosensor of the plurality of magnetic biosensors, and wherein the second plurality of capture antibodies are attached to the bottom surface of the sample container above a second magnetic biosensor of the plurality of magnetic biosensors.

8. The magnetic biosensing system of claim 1, wherein the magnetic moment of the fixed layer of each magnetic biosensor of the plurality of magnetic biosensors in the absence of the external magnetic field is canted out of the major plane of the fixed layer and the magnetic moment of the free layer in the absence of the external magnetic field is oriented parallel to the major plane of the free layer.

9. The magnetic array biosensing system of claim 1, wherein the magnetic moment of the free layer of each magnetic biosensor of the plurality of magnetic biosensors in the absence of the external magnetic field is canted out of the major plane of the free layer and the magnetic moment of the fixed layer in the absence of the external magnetic field is oriented parallel to the major plane of the fixed layer.

10. The magnetic biosensing system of claim 1, further comprising a current source and a voltage source, wherein a magnetic sensor of at least one magnetic biosensor of the plurality of magnetic biosensors further comprises:
   a nonmagnetic layer comprising a first end and a second end, wherein the free layer is formed adjacent to the first end and the fixed layer is formed adjacent to the second end,
   a current source coupling electrically coupled to the free layer, the current source, and the first end of the nonmagnetic layer; and
   a voltage source coupling electrically coupled to the fixed layer, the voltage source, and the second end of the nonmagnetic layer, wherein the voltage source is configured to measure a magnetoresistance of the fixed layer and the second end of the nonmagnetic layer.

11. The magnetic biosensor array of claim 10, wherein the free magnetic layer comprises a plurality of free magnetic layers, wherein the nonmagnetic layer comprises a plurality of first ends, and wherein respective ones of the plurality of free magnetic layers are formed adjacent to respective ones of the plurality of first ends, and wherein each of the free magnetic layers are electrically coupled to the current source.

12. The magnetic biosensing system of claim 1, wherein the probe array further comprises a plurality of sample dispensers configured to dispense solutions into the sample container.

13. A method for forming a magnetic biosensing system, the method comprising:
   forming a probe array comprising a plurality of probes;
   forming a magnetic biosensor array comprising a plurality of electrical contacts located along at least one peripheral edge of the magnetic biosensor array, wherein the plurality of electrical contacts of the magnetic biosensor array are configured to receive respective ones of the plurality of probes;
   placing a sample container over the magnetic biosensor array, wherein the magnetic biosensor array comprises a plurality of magnetic biosensors each located adjacent to a surface of the sample container, each magnetic biosensor of the plurality of magnetic biosensors comprising a magnetic sensor comprising a free layer and a fixed layer, wherein one of the free layer or the fixed layer has a magnetic moment canted out of a major plane of the free layer or the fixed layer at an inclined angle between 1 and 90 degrees, respectively, in an absence of an external magnetic field, and wherein the other of the free layer or the fixed layer has a magnetic moment oriented parallel to the major plane of the free layer or the fixed layer in the absence of the external magnetic field;
   attaching a plurality of capture antibodies to a bottom surface of the sample container above the magnetic stack;
   coupling a motor to the probe array, wherein the motor is configured to move the probe array toward and away from the magnetic biosensor array to engage and disengage the plurality of probes and the plurality of electrical contacts; and
   placing a magnetic field generator below the magnetic biosensor array, wherein the magnetic field generator is configured to apply a magnetic field in a direction perpendicular to a major plane of the magnetic biosensor array.

14. The method of claim 13, wherein forming the magnetic biosensor comprising the magnetic sensor comprising the free layer and the fixed layer comprises:
   forming a nonmagnetic layer comprising a first end and a second end;
   forming the free layer adjacent to the first end;
   forming the fixed layer adjacent to the second end;
   coupling a current source to the free layer and the first end of the nonmagnetic layer; and
   coupling a voltage source to the fixed layer and the second end of the nonmagnetic layer, wherein the voltage source is configured to measure a magnetoresistance of the fixed layer and the second end of the nonmagnetic layer.

* * * * *